(12) United States Patent
Sanborn et al.

(10) Patent No.: US 12,178,550 B2
(45) Date of Patent: Dec. 31, 2024

(54) SYSTEM AND METHOD FOR DISTRIBUTED HEAT FLUX SENSING OF BODY TISSUE

(71) Applicant: INTUITIVE SURGICAL OPERATIONS, INC., Sunnyvale, CA (US)

(72) Inventors: Eric E. Sanborn, Blacksburg, VA (US); Mark E. Froggatt, Blacksburg, VA (US); Jonathan M. Sorger, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1101 days.

(21) Appl. No.: 16/467,950

(22) PCT Filed: Dec. 8, 2017

(86) PCT No.: PCT/US2017/065461
§ 371 (c)(1),
(2) Date: Jun. 7, 2019

(87) PCT Pub. No.: WO2018/107119
PCT Pub. Date: Jun. 14, 2018

(65) Prior Publication Data
US 2020/0069192 A1 Mar. 5, 2020

Related U.S. Application Data

(60) Provisional application No. 62/432,452, filed on Dec. 9, 2016.

(51) Int. Cl.
A61B 5/01 (2006.01)
A61B 5/00 (2006.01)
(Continued)

(52) U.S. Cl.
CPC .............. *A61B 5/015* (2013.01); *A61B 5/685* (2013.01); *G01K 1/026* (2013.01); *G01K 11/32* (2013.01);
(Continued)

(58) Field of Classification Search
None
See application file for complete search history.

(56) References Cited

U.S. PATENT DOCUMENTS 5,166,988 A 11/1992 Bobb et al.
6,380,732 B1 4/2002 Gilboa
(Continued)

FOREIGN PATENT DOCUMENTS

CN 2576191 Y 10/2003
CN 101132730 A 2/2008
(Continued)

OTHER PUBLICATIONS

Office Action mailed Apr. 2, 2021 for Chinese Application No. 201780063607 filed Dec. 8, 2017, 24 pages.
(Continued)

*Primary Examiner* — Sean W Collins
*Assistant Examiner* — Nora W Rhodes
(74) *Attorney, Agent, or Firm* — Haynes & Boone, LLP.

(57) ABSTRACT

A system for distributed heat flux sensing of body tissue includes a distributed sensor, a thermal energy source, and one or more processors. The distributed sensor provides a plurality of temperature measurements corresponding to a plurality of points in a measurement range. The thermal energy source applies thermal energy to the body tissue along the measurement range. The one or more processors are configured to receive the plurality of temperature measurements from the distributed sensor, determine an amount of thermal energy applied by the thermal energy source at
(Continued)

each of the plurality of points, and determine heat flux at each of the plurality of points based on the plurality of temperature measurements and the amount of thermal energy applied by the thermal energy source. The plurality of temperature measurements correspond to the plurality of points.

20 Claims, 14 Drawing Sheets

(51) Int. Cl.
- *A61B 18/00* (2006.01)
- *A61B 18/08* (2006.01)
- *A61B 18/14* (2006.01)
- *G01K 1/02* (2021.01)
- *G01K 11/32* (2021.01)
- *G01K 17/00* (2006.01)
- *A61B 34/20* (2016.01)

(52) U.S. Cl.
CPC .... *G01K 17/00* (2013.01); *A61B 2018/00577* (2013.01); *A61B 2018/00642* (2013.01); *A61B 2018/00666* (2013.01); *A61B 2018/00791* (2013.01); *A61B 2018/00904* (2013.01); *A61B 18/082* (2013.01); *A61B 18/1492* (2013.01); *A61B 2034/2061* (2016.02)

(56) References Cited

U.S. PATENT DOCUMENTS

| | | | |
|---|---|---|---|
| 6,389,187 B1 | 5/2002 | Greenaway et al. | |
| 7,316,681 B2 | 1/2008 | Madhani et al. | |
| 7,772,541 B2 | 8/2010 | Froggatt et al. | |
| 8,050,523 B2* | 11/2011 | Younge | A61B 5/6852 385/13 |
| 8,900,131 B2 | 12/2014 | Chopra et al. | |
| 9,259,274 B2 | 2/2016 | Prisco | |
| 9,452,276 B2 | 9/2016 | Duindam et al. | |
| 2003/0083574 A1 | 5/2003 | Svaasand et al. | |
| 2004/0131504 A1 | 7/2004 | Landers et al. | |
| 2006/0013523 A1 | 1/2006 | Childlers et al. | |
| 2009/0043223 A1 | 2/2009 | Zhang et al. | |
| 2009/0118724 A1* | 5/2009 | Zvuloni | A61N 7/02 601/2 |
| 2009/0326381 A1* | 12/2009 | Yuan | A61B 5/015 600/473 |
| 2010/0056944 A1 | 3/2010 | Keith et al. | |
| 2011/0211665 A1* | 9/2011 | Maurer, Jr. | A61B 6/06 378/19 |
| 2011/0245711 A1* | 10/2011 | Katra | A61B 5/0075 600/547 |
| 2011/0245713 A1* | 10/2011 | Rensen | G01K 7/02 600/549 |
| 2011/0251495 A1* | 10/2011 | Province | A61B 5/01 600/587 |
| 2012/0143176 A1* | 6/2012 | Ryan | A61B 18/24 606/3 |
| 2012/0150031 A1 | 6/2012 | Castella et al. | |
| 2014/0097848 A1 | 4/2014 | Leblanc et al. | |
| 2017/0296268 A1* | 10/2017 | Johnson | A61B 18/14 |
| 2018/0140866 A1* | 5/2018 | Daly | A61B 18/203 |
| 2018/0203040 A1* | 7/2018 | Sadeghian Marnani | G01Q 60/58 |

FOREIGN PATENT DOCUMENTS

| | | |
|---|---|---|
| CN | 101332083 A | 12/2008 |
| CN | 101569523 A | 11/2009 |
| CN | 102209491 A | 10/2011 |
| CN | 102341038 A | 2/2012 |
| CN | 102573691 A | 7/2012 |
| CN | 105377168 A | 3/2016 |
| JP | 2008531170 A | 8/2008 |
| JP | 2012508055 A | 4/2012 |
| JP | 2013043026 A | 3/2013 |
| WO | WO-9220290 A1 | 11/1992 |
| WO | WO-2006092707 A1 | 9/2006 |
| WO | WO-2010055455 A1 | 5/2010 |
| WO | WO-2011048509 A1 | 4/2011 |
| WO | WO-2016099976 A1 | 6/2016 |
| WO | WO-2016191298 A1 | 12/2016 |
| WO | WO-2017155369 A1 * | 9/2017 ......... A61B 5/02055 |

OTHER PUBLICATIONS

Chen T., et al., "Distributed Flow Sensing using Optical Hot-Wire Grid," Optics Express. Apr. 2012, vol. 20(8), pp. 8240-8249.
International Preliminary Report on Patentability for Application No. PCT/US2017/065461, mailed on Jun. 20, 2019, 13 pages.
International Search Report and Written Opinion for Application No. PCT/US2017/065461 mailed on Mar. 28, 2018, 18 pages.
ODISI-B Temperature Sensing, Lunainnovations, [online video], 2013 [retrieved on Dec. 16, 2016] Retrieved from the Internet: https://www.youtube.com/watch?v=obcOMq8ZYQ8.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP22178300.4, mailed on Nov. 17, 2022, 11 pages.

\* cited by examiner

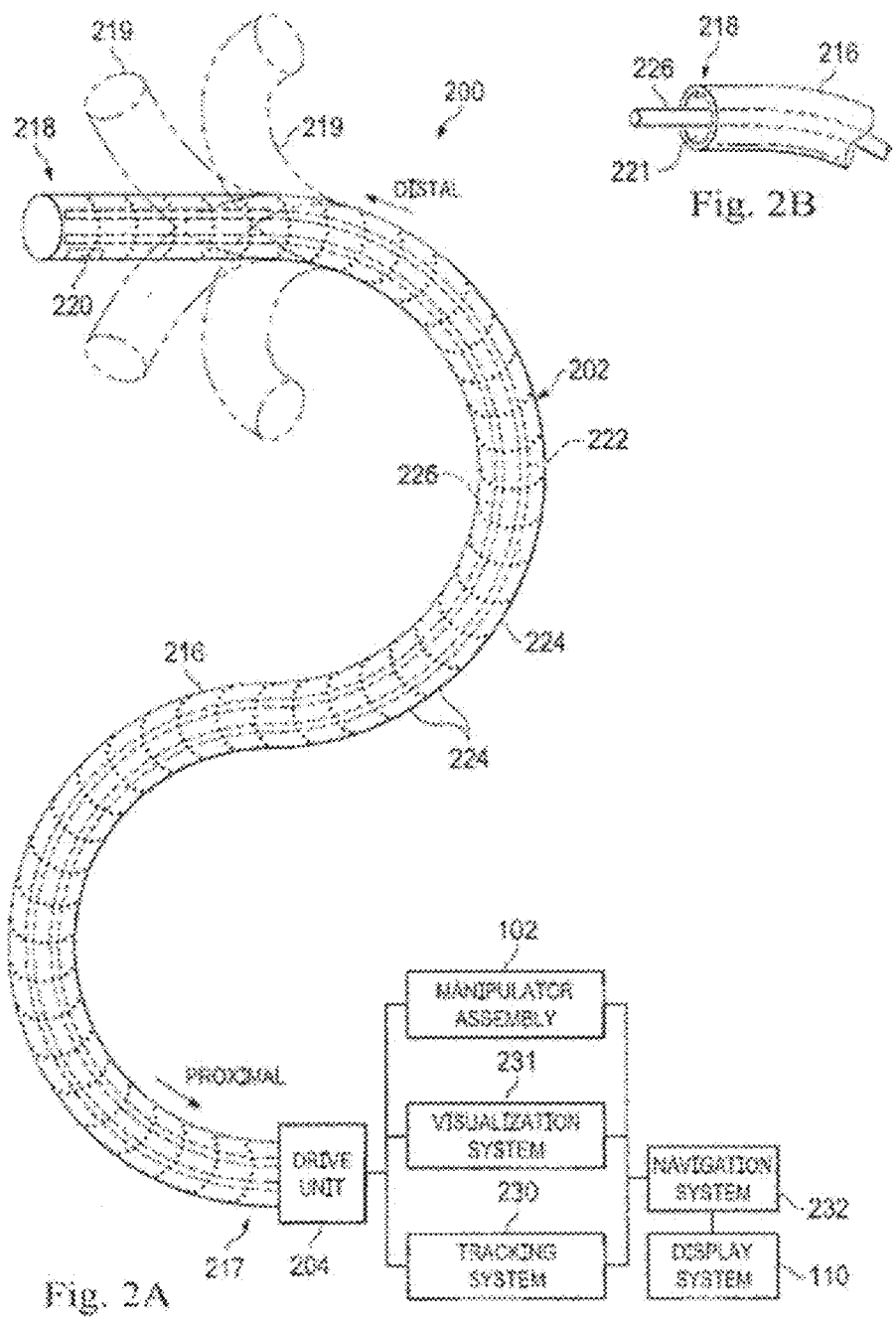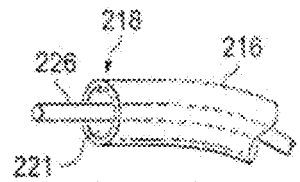
Fig. 2A
Fig. 2B

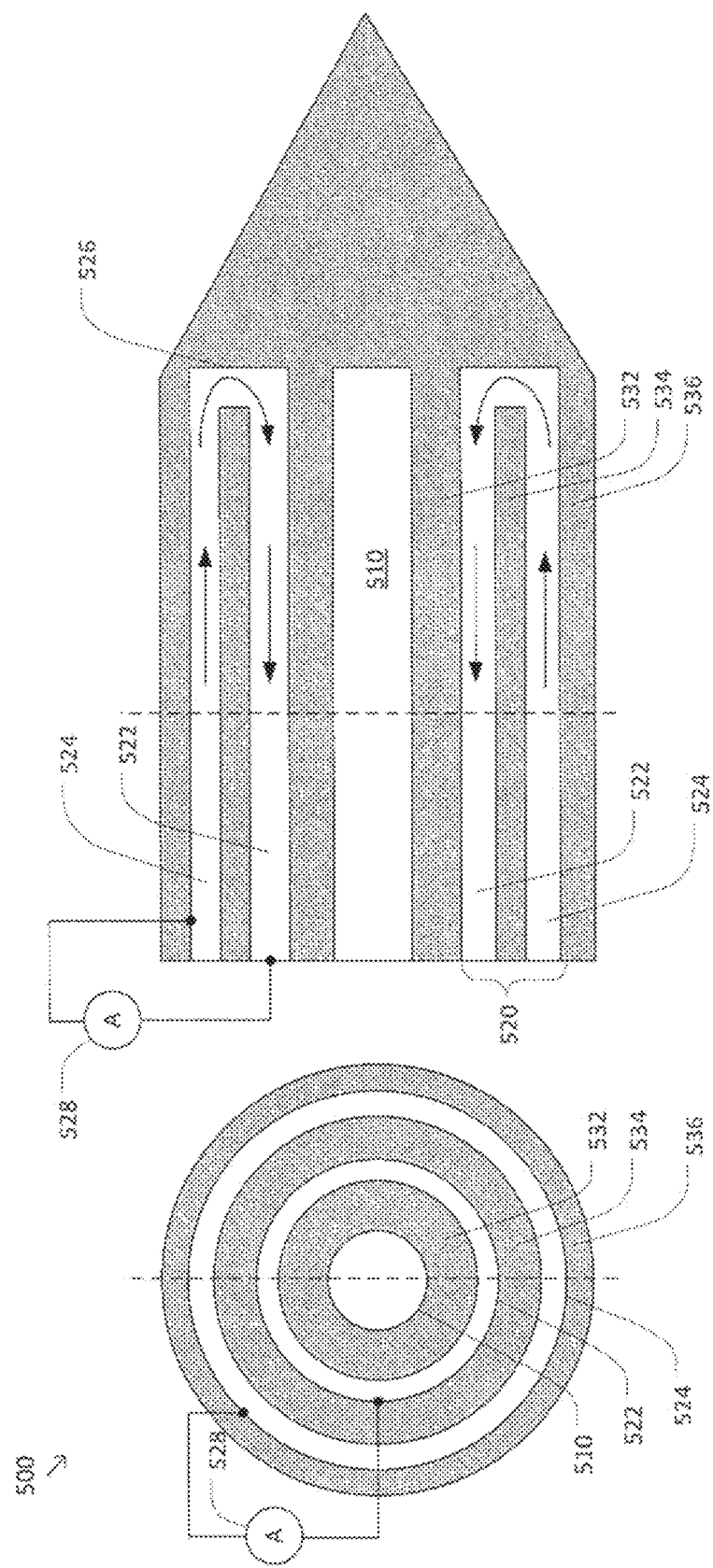

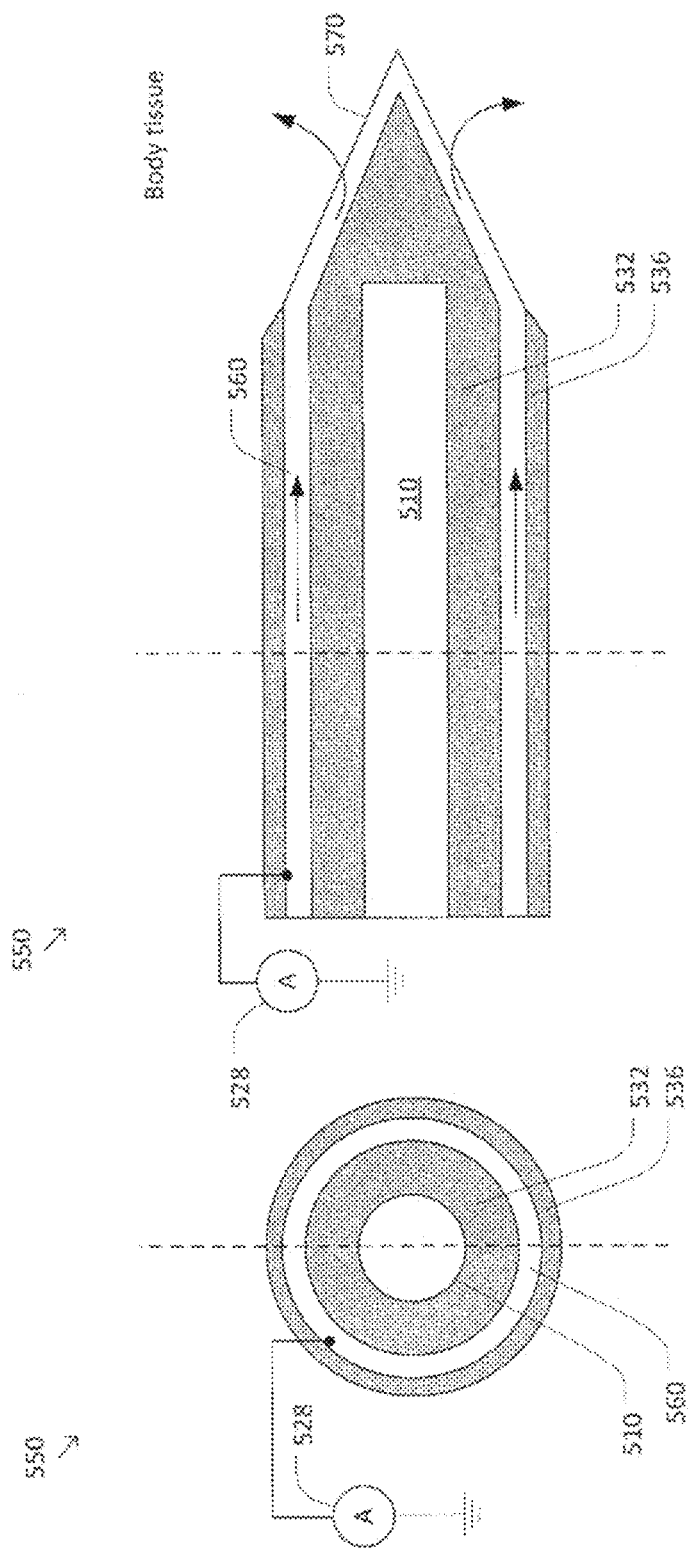

1200

1210 — Provide instructions to insert distributed sensor near targeted tissue of therapeutic procedure 1220 — Provide initial operating parameters to the therapeutic device 1230 — Receive temperature measurements from the distributed sensor 1240 — Provide adjusted operating parameters to the therapeutic device based on the received temperature measurements

FIG. 12

SYSTEM AND METHOD FOR DISTRIBUTED HEAT FLUX SENSING OF BODY TISSUE

RELATED APPLICATIONS

This patent application is a U.S. National Stage patent application of International Patent Application No. PCT/US2017/065461 filed on Dec. 8, 2017, the benefit of which is claimed, and claims priority to and benefit of the filing date of U.S. Provisional Patent Application No. 62/432,452, entitled "System and Method for Distributed Heat Flux Sensing of Body Tissue," filed Dec. 9, 2016, which is incorporated by reference herein in its entirety.

TECHNICAL FIELD

The present disclosure is directed to systems for measuring the heat flux of body tissue and more particularly to a system for distributed heat flux sensing of body tissue.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and one or more medical instruments coupled to the patient-side cart.

Before, after, and/or during the performance of a medical procedure, it is useful to determine properties of body tissue at or near a surgical site. For example, it is useful to determine whether a particular body tissue is healthy, ablated, cancerous or non-cancerous. In addition, it is useful to determine the locations of anatomical features at or near the surgical site. For example, surgical performance may be facilitated by determining a map of the location of blood vessels. Ideally, this information is determined without cutting into the body tissue or extracting tissue from the body.

Before, after, and/or during the performance of a medical procedure, it is also useful to extract real-time feedback from the surgical site. The real-time feedback reflects the impact of the surgical intervention on body tissue at or near a surgical site. For example, when performing a thermal ablation procedure, it is useful to continuously monitor the thermal impact on targeted and non-targeted tissue.

Accordingly, it would be advantageous to provide a system that provides real-time monitoring of a surgical procedure.

SUMMARY

The embodiments of the invention are best summarized by the claims that follow the description.

In some embodiments, a system for distributed heat flux sensing of body tissue may include a distributed sensor, a thermal energy source, and one or more processors. The distributed sensor provides a plurality of temperature measurements corresponding to a plurality of points in a measurement range. The thermal energy source applies thermal energy to the body tissue along the measurement range. The one or more processors are configured to receive the plurality of temperature measurements from the distributed sensor, determine an amount of thermal energy applied by the thermal energy source at each of the plurality of points, and determine heat flux at each of the plurality of points based on the plurality of temperature measurements and the amount of thermal energy applied by the thermal energy source. The plurality of temperature measurements correspond to the plurality of points.

In some embodiments, a method for determining heat flux of body tissue using a distributed sensor may include receiving a plurality of temperature measurements from the distributed sensor, determining an amount of applied thermal energy at the plurality of points, and determining a heat flux of the body tissue at a plurality of points based on the received plurality of temperature measurements and the determined amount of applied thermal energy. The plurality of temperature measurements correspond to the plurality of points in a measurement range of the distributed sensor.

In some embodiments, a method for providing feedback to an ablation system using a distributed heat flux sensor may include providing initial operating parameters to an ablation probe to perform an ablation procedure, receiving a plurality of heat flux measurements from the distributed heat flux sensor captured during the ablation procedure, and providing adjusted operating parameters to the ablation probe based on the plurality of heat flux measurements.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 2A is a simplified diagram of a medical instrument system utilizing aspects of the present disclosure.

FIG. 2B is a simplified diagram of a medical instrument with an extended medical tool according to some embodiments.

FIGS. 5 A-D are simplified cross-sectional diagrams of a distributed heat flux sensor in a concentric arrangement according to some embodiments.

FIG. 12 is a simplified diagram of a method of providing feedback during a therapeutic procedure according to some embodiments.

DETAILED DESCRIPTION

Figure 1:
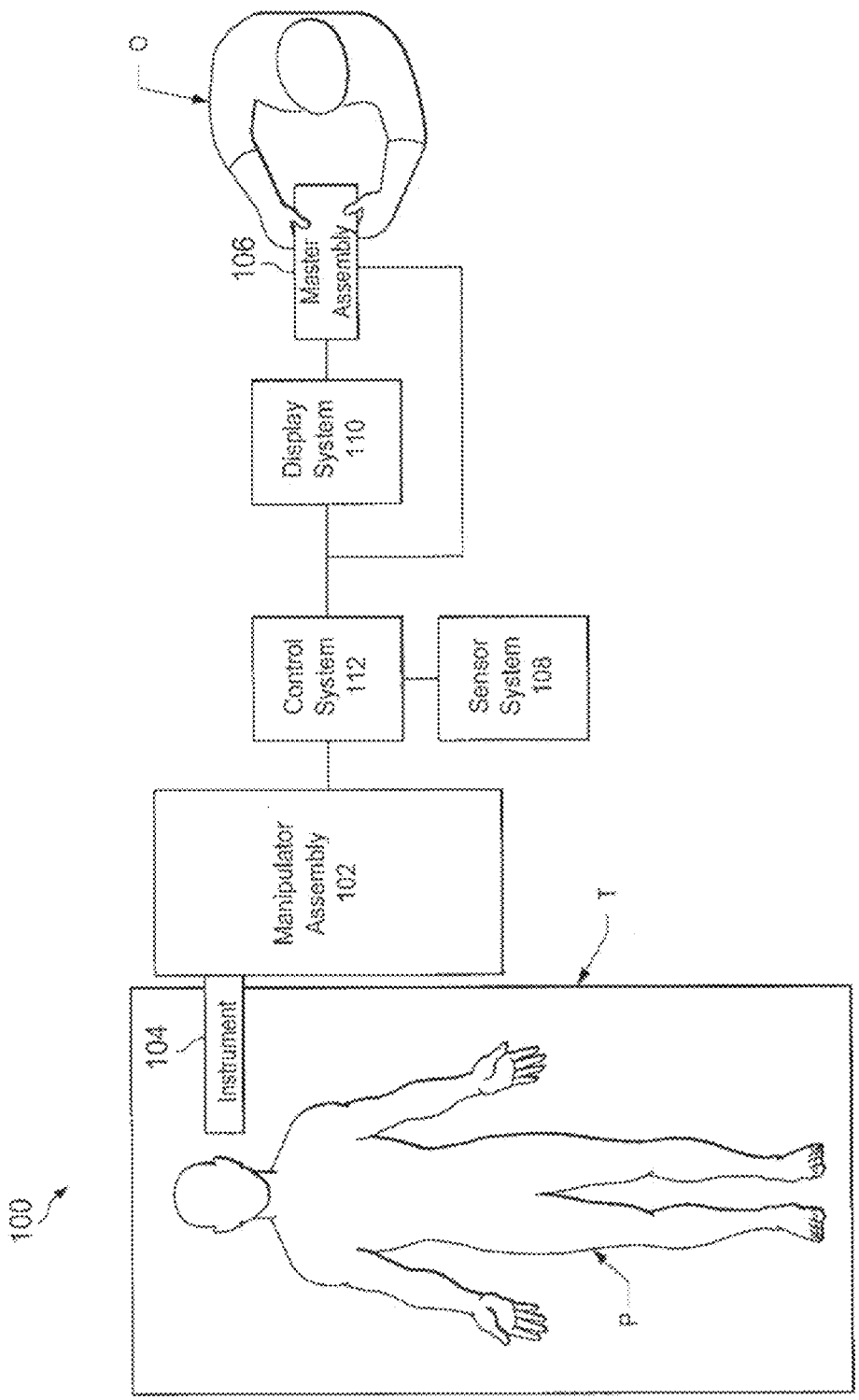
FIG. 1 is a simplified diagram of a teleoperated medical system, in accordance with embodiments of the present disclosure.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom that can be described using changes in Cartesian X, Y, Z coordinates, such as along Cartesian X, Y, Z axes). As used herein, the term "orientation" refers to the rotational placement of an object or a portion of an object (three degrees of rotational freedom—e.g., which can be described using roll, pitch, and yaw). As used herein, the term "pose" refers to the position of an object or a portion of an object in at least one degree of translational freedom, and to the orientation of that object or that portion of that object in at least one degree of rotational freedom. For an asymmetric, rigid body in a three-dimensional space, a full pose can be described with six total degrees of freedom.

Also, although some of the examples described herein refer to surgical procedures or tools, or medical procedures and medical tools, the techniques disclosed apply to non-medical procedures and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical, medical treatment or diagnosis procedures.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a manipulator assembly 102 for operating a medical instrument 104 in performing various procedures on a patient P. Manipulator assembly may be teleoperated or may include both teleoperational and non-teleoperational sub-assemblies for manual, robotic, and/or teleoperated control of medical instrument 104. Manipulator assembly 102 is mounted to or near an operating table T. An operator input system such as a master assembly 106 allows an operator O (e.g., a surgeon, a clinician, or a physician as illustrated in FIG. 1) to view the interventional site and to control manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Manipulator assembly 102 or more specifically the teleoperational manipulator may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112. The processors of the control system 112 may execute instructions corresponding to methods and operators described herein.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter the data points. In some embodiments, a virtual navigational image may be presented in the display 110 that depicts a model of an anatomical passageway from a perspective of an instrument being inserted along or through a corresponding actual anatomical passageway.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. The optical fiber of the shape sensor system 222 may enable the simultaneous collection of a set of measured points that describe the positions of various portions of the shape sensor 222 along the length of the flexible catheter body 216 at a single point in time. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties.

Sensors in some embodiments may employ other suitable strain sensing techniques, such as Rayleigh scattering, Raman scattering, Brillouin scattering, and fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor 222 may also function as the position sensor because the shape of the sensor 222 together with information about the location of the base of the shape sensor 222 (in the fixed coordinate system of the patient, referred to as "patient space") allows the location of various points along the shape sensor, including the distal tip, to be calculated.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static. The tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3:
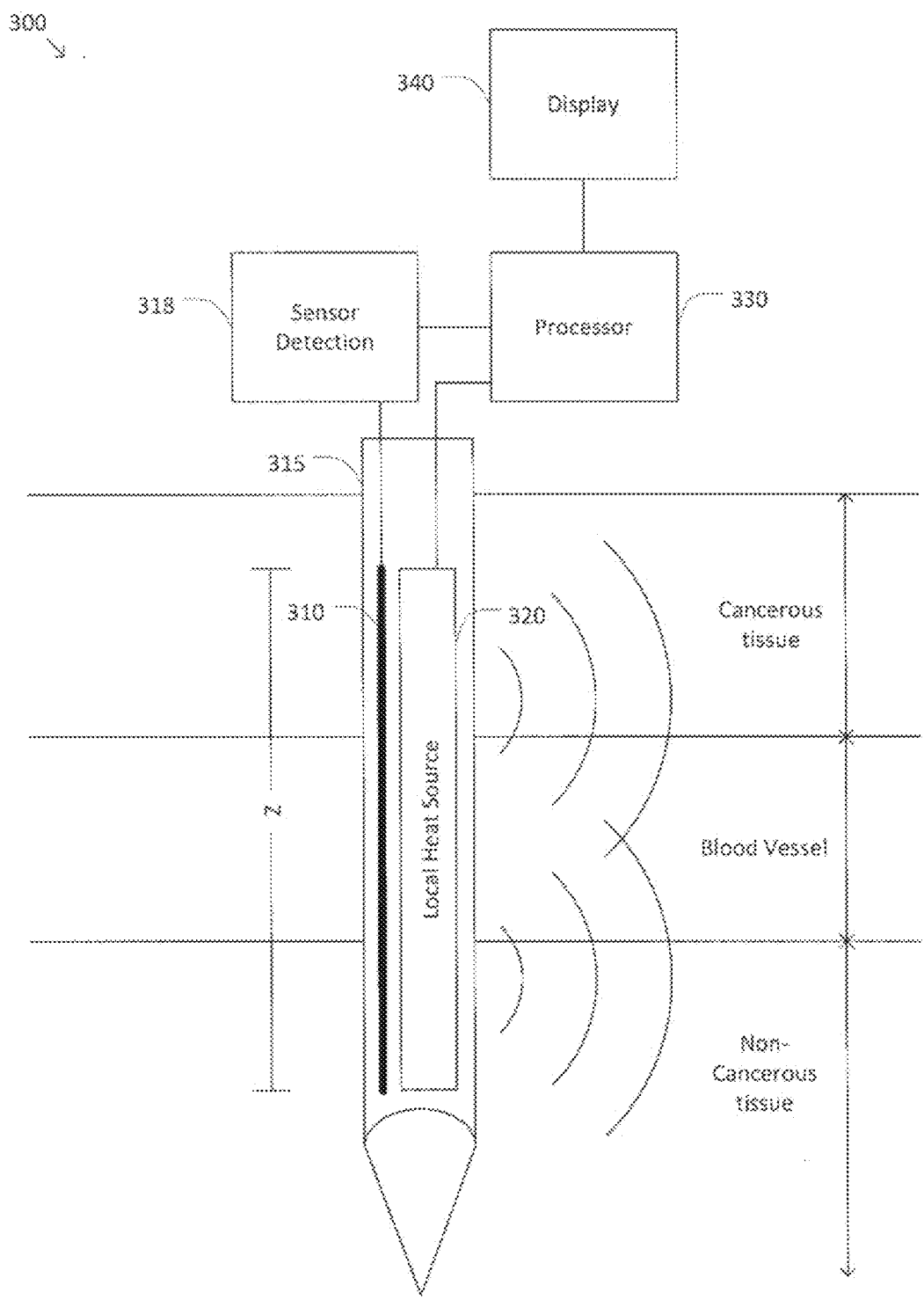
FIG. 3 is a simplified diagram of a distributed heat flux sensor system according to some embodiments.

FIG. 3 is a simplified diagram of distributed heat flux sensor system 300 according to some embodiments. According to some embodiments consistent with FIGS. 1-2, distributed heat flux sensor system 300 may be a component of a medical system, such as teleoperated medical system 100 and/or medical instrument system 200. Distributed heat flux sensor system 300 is capable of providing information to help resolve spatial variations in the heat flux of body tissue. This information may be used to identify the type of body tissue, the health of body tissue, and/or the condition of body tissue. The location of the body tissue and anatomical features can also be determined as will be described in more detail below. In some examples, distributed heat flux sensor system 300 may be used for identifying a type of body tissue, such as lung tissue, a specific layer of lung tissue, blood vessels, or tissue of other organs such as heart, liver, diaphragm tissue, and/or the like. In some examples, the information from the distributed heat flux sensor system 300 may be used for diagnostic purposes, determining the health of tissue, such as for determining whether tissue is cancerous, non-cancerous, healthy, or unhealthy (e.g. inflamed, infected, necrosed, etc.). In some examples, the information may be used to identify condition of tissue, such as ablated or non-ablated. In some examples, distributed heat flux sensor system 300 may be used in preparation for a surgical procedure, e.g., by providing a map of the location of blood vessels. In some examples, distributed heat flux sensor system 300 may be used for real-time monitoring during the performance of a surgical procedure, e.g., by determining whether targeted tissue has been successfully ablated during the performance of an ablation procedure. In each application, the distributed heat flux sensor system 300 may be able to probe the characteristics of the body tissue with little physical intrusion, e.g., without cutting into the body tissue and/or extracting tissue from the body. For example, the distributed heat flux sensor system 300 may probe the body tissue via needle insertion, through minimally invasive access through a natural orifice or artificial opening, and/or the like.

The sensor system 300 includes a distributed sensor 310 housed in, mounted to, or otherwise coupled to an instrument 315, which may be, for example, a needle, an endoscopic probe, an ablation probe, a catheter, a stapler, a clip applier, a needle driver, a grasper, a retractor, scissors, shears, a scalpel, a stapler, a cautery device, a vessel sealer, or any of a variety of surgical, diagnostic, therapeutic, delivery, or biopsy instruments. During operation, Instrument 315 is positioned in thermal contact with body tissue to measure temperature at a plurality of points along a measurement range Z. For example, thermal contact may be achieved by inserting instrument 315 into the body tissue, placing instrument 315 in direct contact with a surface of the body tissue, and/or otherwise positioning instrument 315 sufficiently close to the body tissue to determine the temperature with the desired accuracy. The instrument 315 may be rigidly straight, flexible, steerable, and/or curved and while shown as being inserted within tissue in a direct insertion path, the insertion path within measurement range Z may be curved in any pattern necessary to traverse the tissue and avoid any anatomical structures which should not be punctured. The measurement range Z may extend through one or more types of biological tissues, including cancerous and non-cancerous tissue, ablated tissue, healthy tissue, blood vessels, nerves, and/or other anatomical structures or varying layers of tissue. As depicted in FIG. 3, the measurement range Z is illustrated spanning regions corresponding to cancerous tissue, a blood vessel, and non-cancerous tissue.

According to some embodiments, distributed sensor 310 may include a fiber optic sensor. In various embodiments a fiber optic sensor may include Fiber Bragg Gratings (FBG) to provide distributed strain and/or temperature measurements along the length of an optical fiber. An example of a fiber optic sensor is described in U.S. patent application Ser. No. 11/180,389 filed on Jul. 13, 2005, the disclosure of which is incorporated herein in its entirety.

In one embodiment, the fiber optic sensor may include one or more cores contained within a single cladding. An array of Fiber Bragg Gratings is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBGs, the modulations are spaced by a known distance, thereby causing reflection of a known band of wavelengths. As a grating encounters environmental conditions such as temperature or strain, the fiber becomes compressed or stretched. These changes in the fiber modify the refractive index profile and, consequently, the spectral response of the FBGs. The change in the spectral response can be interpreted to determine the stimulus for the change.

There are a variety of ways of multiplexing the Fiber Bragg Gratings so that a single fiber core can carry many sensors and the readings of each sensor can be distinguished. For example, wavelength division multiplexing (WDM) may be used to distinguish among the readings. In some examples, the temperature along the length of an optical fiber may be determined using optical frequency domain reflectometry (OFDR) and/or optical time domain reflectometry (OTDR). A continuous measure of temperature along the length of the fiber optic sensor may be derived by interpreting the optical response of the core using swept wavelength inteferometry. OFDR, for example, may enable temperature detection from hundreds or thousands of FBG distributed along a single fiber core. According to some embodiments, the fiber optic sensor may achieve sub-1 mm spatial resolution. According to some embodiments, the diameter of the fiber optic sensor may be 200 microns or less.

In some embodiments, the fiber optic sensor may additionally determine a shape of the sensor. For example, the fiber optic sensor may concurrently determine the temperature and three dimensional shape of the sensor using a multicore optical fiber, at least one of the cores forming a fiber optic bend sensor, as discussed above with respect to FIG. 2. An example of a multicore optical fiber for shape and temperature measurements is described in International Pat. App. No. PCT/US2015/064213 filed on Dec. 7, 2015, the disclosure of which is incorporated herein in its entirety. Shape data and temperature data may be combined to determine the three-dimensional position of each temperature measurement obtained using the fiber optic sensor.

The sensor system 300 may also include a sensor detection system 318 coupled to the distributed sensor 310. The sensor detection system 318 generates and detects the reflected light used for determining the temperature and/or shape along the measurement range Z. Thus, the sensor detection system 318 can determine the shape and/or position, location, orientation, and/or pose of the distributed sensor in a known reference frame. The sensor detection system may comprise an optical source, an optical detector, and a demodulator.

The sensor system 300 may also include a local heat source 320 that is positioned in thermal contact with the body tissue. Local heat source 320 applies heat to the body tissue within a detectable range of distributed sensor 310 such that distributed sensor 310 measures an effect of local heat source 320 on the temperature of the body tissue. For example, local heat source 320 may apply heat to the body tissue that is directly adjacent to the distributed sensor. In this example, local heat source 320 may be mounted to the same instrument 315 as the distributed sensor 310. Alternatively the local heat source 320 may be positioned near and substantially in parallel to distributed sensor 310. In one example, the local heat source 320 may include a conductive cladding that wraps fully or partially around distributed sensor 310. The conductive cladding becomes heated upon application of electric current. In some examples, local heat source 320 and distributed sensor 310 may be the same device.

The output power level of local heat source 320 is selected to cause a measurable change in the temperature of the body tissue within a detectable range of distributed sensor 310 along the measurement range Z (e.g., body tissue within 2 mm of distributed sensor 310) without altering or damaging the body tissue. Accordingly, the output power level for a given procedure may be determined empirically, as the desired level may vary based on the type of body tissue under investigation and/or other operating conditions. In general, the output power level of local heat source 320 is substantially less than that of instruments, such as ablation tools, that operate to destroy tissue by applying thermal energy.

In some examples, when distributed sensor 310 includes a fiber optic sensor, heating illumination may be applied through the optical fiber to cause the fiber to heat up and/or to radiate heat into neighboring tissue. The heating illumination may have a wavelength that is different from the wavelength of the illumination used for determining the temperature. For example, the wavelength of the heating illumination may correspond to a portion of the transmission spectrum of the optical fiber with low transmission. In an illustrative example, the optical fiber may include a glass cladding made from fused silica, which absorbs illumination with a wavelength of 2200 nm. Accordingly, heating illumination with a wavelength of 2200 nm may be launched into the cladding of the optical fiber to heat the fiber via absorption of the heating illumination. Meanwhile, illumination used for determining the temperature of the fiber may be launched into the core of the optical fiber. Although the heating of the optical fiber may be non-uniform (e.g., non-linear) as a function of distance along the fiber, such non-uniformity may be accounted for during processing, e.g., using a pre-determined calibration curve that adjusts the results to compensate for the non-uniformity caused by non-uniform heating.

In some examples, heat may be applied to the body tissue by generating standing electromagnetic waves inside the fiber optic sensor, causing the fiber to heat up. For example, the fiber optic sensor may be coated in a conductive material, such as a metal, to support standing waves inside the fiber. Consistent with such embodiments, distributed heat flux sensor system 300 may include an RF generator to generate the standing wave in the fiber.

In some examples, the fiber optic sensor may include one or more conductive fibers and/or cores. For example, a fiber may be drawn with a semiconductor or metal material such that one or more cores of the fiber are conductive. Accordingly, heat may be applied to the body tissue by resistively heating the conductive fiber.

Local heat source 320 may be omitted in some embodiments. Additionally or alternatively, distributed heat flux sensor system 300 may include a remote heat source, such as an ablation probe as discussed below with reference to FIG. 9, a heat source from a tool such as a vessel sealer, cautery device, or hot shears, and/or a heat source located outside of the body that radiates thermal energy into the body tissue by electromagnetic radiation, acoustic waves, and/or the like. In some examples, the distributed heat flux sensor system 300 may include a local or remote thermal energy source that cools, rather than heats, the body tissue.

The sensor system 300 also includes a processor 330 coupled the sensor detection system 312 to receive a plurality of temperature measurements corresponding to points in the measurement range Z of the distributed sensor 310. Processor 330 may further determine a three-dimensional location of each of the corresponding points in a known reference frame. The plurality of temperature measurements may be received concurrently or sequentially and separately. Processor 330 may further determine the amount of thermal energy applied by local heat source 320 at the plurality of points. For example, the amount of applied thermal energy at each point may be a constant value, a known variable value, a user-provided parameter, a parameter provided by local heat source 320, and/or the like. In some examples, processor 330 may be coupled to local heat source 320 to receive a signal indicating the amount of applied heat and/or to control the amount of applied heat.

Processor 330 determines the heat flux at each of the plurality of points in the measurement range Z based on the received temperature measurements and the determined amount of applied heat. According to some embodiments, the heat flux may be determined based on the maximum amount of heat that can be applied to the tissue without a corresponding rise in the temperature of the tissue. That is, the heat flux is determined based on the point where the amount of heat applied to an affected volume of tissue by local heat source 320 matches the amount of heat being conducted away from the affected volume by the tissue. In some examples, processor 330 may identify the type of tissue corresponding to the determined profile of heat flux. For example, processor 330 may include and/or may be in communication with a database (or other data structure) that identifies types of tissue and/or other anatomical features based on their heat flux profile. Consistent with such embodiments, processor 330 may predict the type of tissue and/or anatomical feature at each point in the measurement range by looking up the type of tissue or anatomical feature that corresponds to a given heat flux in the database.

Processor 330 may also determine the three-dimensional location of each of the heat flux measurements within the patient's body. For example, processor 330 may receive shape data from the fiber optic sensor and determine the three-dimensional location based on the shape data in a known reference frame. Based on the three-dimensional location in the known reference frame, and registration of the known reference frame with a patient reference frame and/or imaging reference frame, processor 330 may overlay the heat flux measurements onto images of the patient's body (e.g., endoscope images, CT images and/or virtual navigational images, as discussed above with respect to FIG. 1), track changes in the heat flux at a given location over time, and/or the like.

The sensor system 300 also includes a display 340, such as display system 110, that may be viewable by a user, such as a surgeon or other operator of distributed heat flux sensor system 300. For example, display 340 may be incorporated into an operator's console and/or a master assembly, such as master assembly 106. According to some embodiments, display 340 may be coupled to processor 330 and may depict a visual representation of the determined heat flux at each of the plurality of points in the measurement range Z. In some examples, the visual representation may include a plot of heat flux as a function of position along the measurement range Z. In some examples, the visual representation may include alphanumeric text, such as a spreadsheet, that identifies heat flux as a function of position along the measurement range Z. In some examples, the visual representation may include images of the patient's body with superimposed heat flux information. For example, anatomical features in the images may be color coded based on the measured heat flux. In some examples, display 340 may provide visual, audio, and/or haptic alerts to the user. For example, display 340 may alert the user when the heat flux exceeds (and/or drops below) a threshold or enters a target range. The alert may indicate, for instance, that instrument 315 has reached a target area and/or has entered a danger area and instrument forward movement should be ceased or the instrument should be retracted. In some examples, display 340 may instruct the user to adjust the parameters of one or more medical instruments (e.g., an ablation probe as discussed below with reference to FIG. 7) and/or alter the performance of a medical procedure (e.g., an ablation procedure) based on the determined heat flux.

Figure 4:
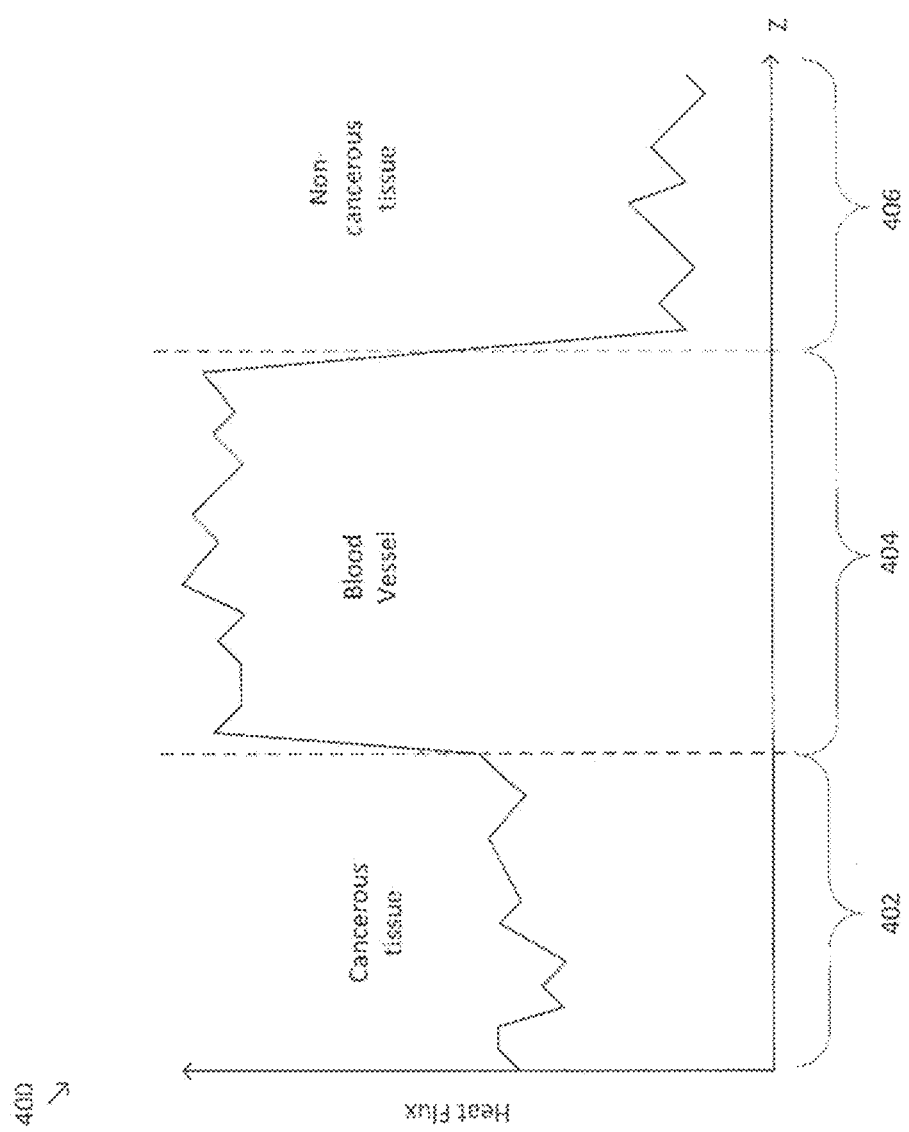
FIG. 4 is a simplified diagram of a plot that represents heat flux as a function of position.

FIG. 4 is a simplified diagram of a plot 400 that represents heat flux along a measurement range Z. In some examples consistent with FIG. 3, plot 400 may depict measurement data determined using distributed heat flux sensor system 300 and may be displayed to a user via display 340. As depicted in plot 400, the measurement range 404 corresponding to a blood vessel has the highest heat flux, as blood flow in the blood vessel is greater than within other types of tissue. By contrast, the non-cancerous tissue in the measurement range 406 may have the lowest heat flux, as there is little blood flow through the non-cancerous tissue. Cancerous tissue in the measurement range 402 has an intermediate heat flux, as there is typically greater blood flow through cancerous tissue than non-cancerous tissue. Although not depicted in plot 400, various types of tissue other than cancerous and non-cancerous tissues and blood vessels may be distinguished in a similar manner. For example, healthy tissue may have a greater blood flow and corresponding greater heat flux than ablated tissue. Although plot 400 is depicted with a relatively noisy signal, it is to be understood that various signal processing techniques may be applied to the raw measurement data to smooth out the data.

FIGS. 5 A & B are simplified cross-sectional diagrams of a distributed heat flux sensor 500 in a concentric, bipolar arrangement according to some embodiments. According to some embodiments consistent with FIG. 3, distributed heat flux sensor 500 may be used to implement distributed sensor 310, instrument 315, and/or local heat source 320. In some embodiments, distributed heat flux sensor 500 may have a very small diameter, e.g., 400 microns or less, to facilitate insertion into and/or near body tissue with minimal tissue damage.

A distributed temperature sensor 510 is positioned in the center of distributed heat flux sensor 500. Distributed temperature sensor 510 generally corresponds to distributed sensor 310, as described above with respect to FIG. 3. Accordingly, distributed temperature sensor 510 may be a fiber optic sensor.

A conductive cladding 520 is disposed concentrically around distributed temperature sensor 510. Conductive cladding 520 is used to implement local heat source 320, as described above with respect to FIG. 3. Conductive cladding 520 includes an inner conductor 522 and an outer conductor 524. Inner conductor 522 and outer conductor 524 are coupled at a tip 526 of distributed heat flux sensor 500 to form an electrical circuit. A current source 528 provides electrical current to cause inner conductor 522 and/or outer conductor 524 to generate heat via resistive heating. Current source 528 may be a DC current source, AC current source, pulsed current source, and/or the like. Current source 528 may be controlled manually by a user and/or automatically by a processor, such as processor 330.

Distributed heat flux sensor 500 may include one or more insulating layers 532, 534, and/or 536 to prevent or reduce leakage of electrical current from conductive cladding 520. For example, outer insulating layer 536 may include a Kapton coating over outer conductor 524 to block current from being shunted into the body. Likewise, inner insulating layer 532 may electrically separate inner conductor 522 from distributed temperature sensor 510. However, in some examples inner insulating layer 532 may be omitted. For example, inner conductor 522 may be in direct contact with distributed temperature sensor 510 (e.g., when inner conductor 522 is formed as a conductive coating on a fiber optic sensor).

A spacing insulator layer 534 separates inner conductor 522 and outer conductor 524. According to some embodiments, spacing layer 534 may be an air gap between inner conductor 522 and outer conductor 524. For example, spacing layer 534 may be an air gap when inner conductor 522 and outer conductor 524 are each formed using metal tubes. Alternately or additionally, spacing layer 534 may include an insulating tube, such as a glass capillary. Consistent with such embodiments, inner conductor 522 and outer conductor 524 may be formed by coating the inner and outer surfaces of the glass capillary with a conductive material, such as a carbon coating. The thickness of carbon coating may be selected to provide a large resistance to efficiently convert electrical current into heat. For example, the thickness of the carbon coating may be 10 nm or less.

FIGS. 5 C & D are simplified cross-sectional diagrams of a distributed heat flux sensor 550 in a concentric, monopolar arrangement according to some embodiments. Distributed heat flux sensor 550 generally provides the same or similar functionality as distributed heat flux sensor 500. Unlike distributed heat flux sensor 500, however, distributed heat flux sensor 550 includes a conductive cladding 560 without a return current path. Instead, distributed heat flux sensor 500 includes a body electrode 570 at the tip of distributed heat flux sensor 500 that forms an electrical contact between conductive cladding 560 and the body tissue. Accordingly, the body provides a return path for the heating current supplied by current source 528. Because conductive cladding 560 has fewer conductive layers than conductive cladding 520, distributed heat flux sensor 550 may have a smaller diameter than distributed heat flux sensor 500. Moreover, conductive cladding 560 may offer improved heat conduction relative to conductive cladding 520 due to having fewer and/or thinner layers, thereby increasing the sensitivity and/or accuracy of distributed temperature sensor 510 to the temperature outside of conductive cladding 560.

Figures 6A, 6B:
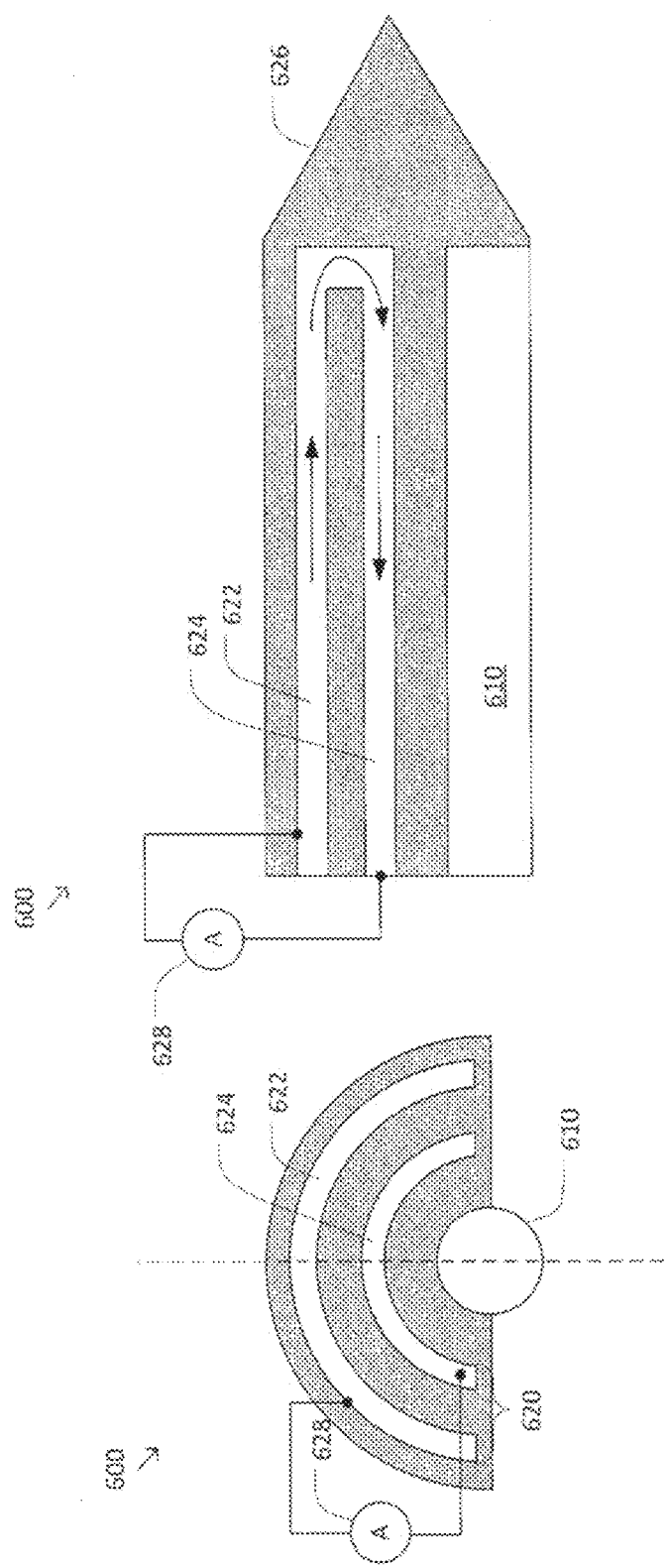
FIGS. 6 A & B are simplified cross-sectional diagrams of a distributed heat flux sensor in a semi-concentric arrangement according to some embodiments.

FIGS. 6 A & B are simplified cross-sectional diagrams of a distributed heat flux sensor 600 in a semi-concentric arrangement according to some embodiments. Distributed heat flux sensor 600 generally provides the same or similar functionality as distributed heat flux sensors 500 and/or 550, as discussed previously with respect to FIG. 5. In particular, distributed heat flux sensor 600 includes a distributed temperature sensor 610, a conductive cladding 620, an inner conductor 622, an outer conductor 624, a tip 626, a current source 628, and an insulator 630, which generally correspond to similarly labeled elements of FIG. 5. Although conductive cladding 620 is depicted in a bipolar arrangement, similar to conductive cladding 520, it is to be understood that conductive cladding 620 may also be configured in a monopolar arrangement, similar to conductive cladding 560.

Unlike distributed heat flux sensor 500, however, distributed heat flux sensor 600 is configured in a semi-concentric arrangement in which distributed temperature sensor 610 is not fully enclosed by conductive cladding 620. The semi-concentric arrangement provides an interface for direct contact between distributed temperature sensor 610 and the body tissue. Thus, in some embodiments, distributed heat flux sensor 600 may achieve improved measurement accuracy and/or responsiveness relative to distributed heat flux sensor 500.

Figure 7B:
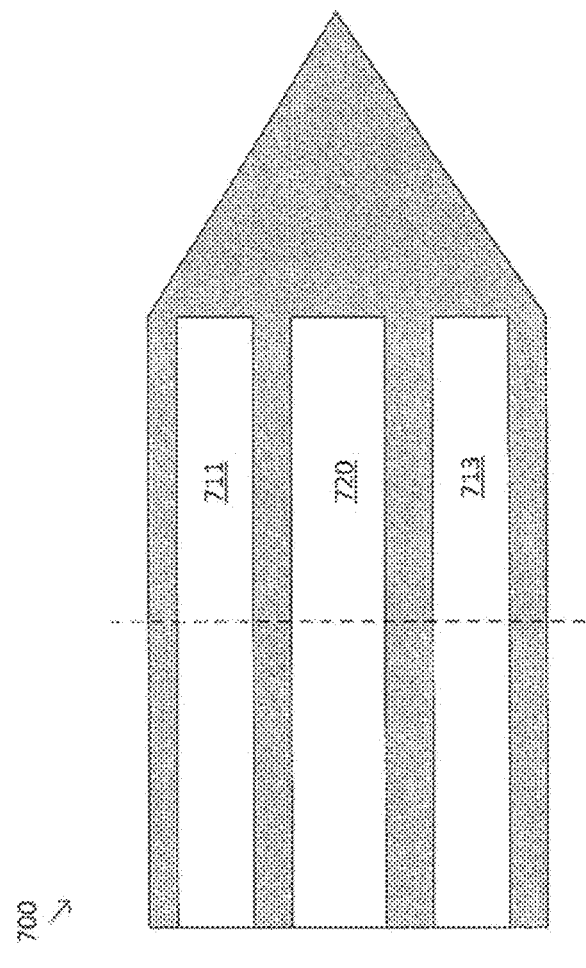
FIGS. 7 A & B are simplified cross-sectional diagrams of a distributed heat flux sensor in a multi-fiber arrangement according to some embodiments.
Figure 7A:
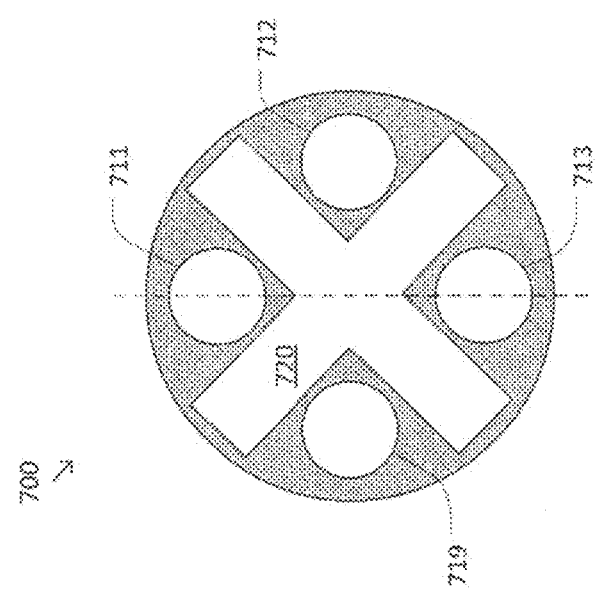

FIGS. 7 A & B are simplified cross-sectional diagrams of a distributed heat flux sensor 700 in a multi-fiber arrangement according to some embodiments. Distributed heat flux sensor 700 generally provides similar functionality to distributed heat flux sensors 500 and/or 600, as discussed previously with respect to FIGS. 5 & 6. However, distributed heat flux sensor 700 includes a plurality of distributed temperature sensors 711-719 rather than a single distributed temperature sensor. A cross-shaped local heat source 720 is disposed between distributed temperature sensors 711-719, such that each of distributed temperature sensors 711-719 is disposed in a different quadrant of local heat source 720. Accordingly, each of distributed temperature sensors 711-719 measures the body tissue temperature on a different side of heat flux sensor 700. Distributed heat flux sensor 700 may be used to determine differentials, gradients, and/or other directional information associated with the heat flux. Although four distributed temperature sensors 711-719 are depicted in FIG. 7, it is to be understood that any number of distributed temperature sensors may be used.

In some examples, local heat source 720 may be omitted from distributed heat flux sensor 700. For example, local heat source 720 may be substituted with a thermal insulator. Consistent with such embodiments, distributed heat flux sensor 700 may function as a distributed temperature sensor with directional sensitivity (e.g., four quadrant sensitivity). A remote thermal energy source may be used to supply thermal energy to tissue in the vicinity of the distributed temperature sensor for heat flux measurement applications.

Figure 8:
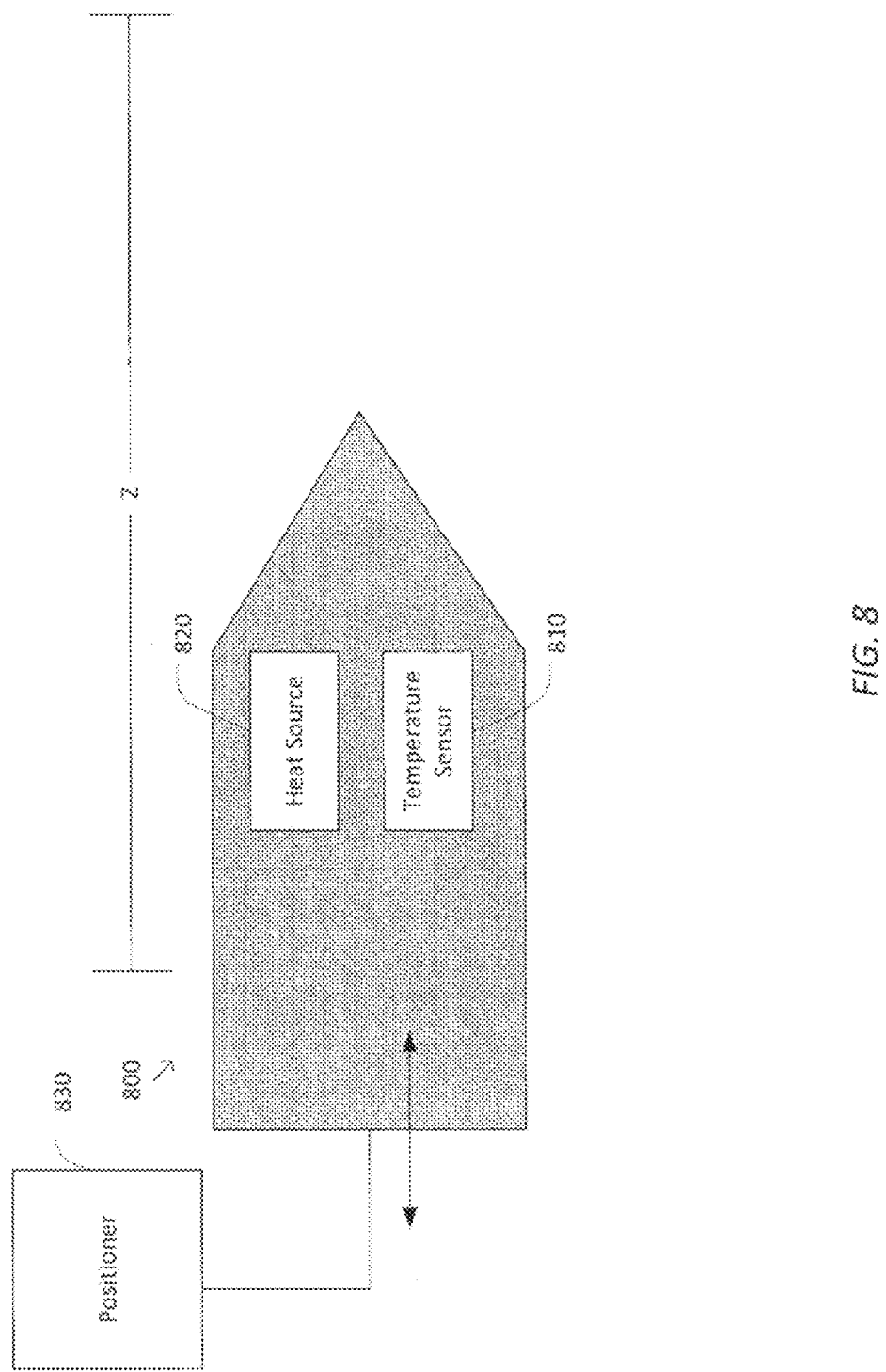
FIG. 8 is a simplified diagram of a distributed heat flux sensor in a scanning mode arrangement according to some embodiments.

FIG. 8 is a simplified diagram of a distributed heat flux sensor 800 in a scanning mode arrangement according to some embodiments. Distributed heat flux sensor 800 generally provides similar functionality to distributed heat flux sensors 500, 600, and 700, as discussed previously with respect to FIGS. 5-7. However, whereas distributed heat flux sensors 500, 600, and 700 generally measure heat flux along each point in the measurement range Z in a batch mode (e.g., the heat flux is measured at each point concurrently and/or without physically repositioning the sensor), distributed heat flux sensor 800 measures temperature in a scanning mode, i.e., by physically moving a temperature sensor 810 and/or a heat source 820 through the measurement range Z. In some embodiments, distributed heat flux sensor 800 may be mounted to otherwise integrated into an instrument such as a catheter, probe, needle, ablation tool, biopsy tool, or any similar device.

In some examples, temperature sensor 810 may be a distributed temperature sensor, such as a fiber optic sensor. Information obtained by physically moving the fiber optic sensor through the measurement range Z may be used to compensate for spatial non-uniformities in the measurement sensitivity of fiber optic sensor and/or the distribution of heat applied by heat source 810. For example, the scanning mode may be used to determine a calibration curve for distributed heat flux sensor 800.

In some examples, temperature sensor 810 may be a point temperature sensor, such as an extrinsic Fabry-Perot interferometer (EFPI)-based temperature sensor. The EFPI-based temperature sensor is extremely sensitive to small changes in optical path length caused by temperature variations in point temperature sensor 810. Consistent with such embodiments, heat source 820 may be a point heat source that is coupled to the point temperature sensor. Accordingly, the point heat source moves through the measurement range Z along with the point temperature sensor. In some examples, however, the point heat source may move independently of the point temperature sensor. In some embodiments, distributed heat flux sensor 800 may include other means for heating the body tissue, such as an elongate heating source that applies heat throughout the measurement range without physical repositioning.

In various examples, the movement (e.g., insertion) of the sensor 800 (or the instrument to which it is mounted) may be controlled by a positioner 830 such as manipulator assembly 102. For example, positioner 830 may automatically move (e.g. insert/withdraw/steer) sensor 800 (e.g. temperature sensor 810 and/or heat source 820) through the measurement range Z, positioner 830 may include a teleoperated actuation mechanism for inserting, withdrawing and/or articulating sensor 800, or the sensor 800 may be manually inserted/withdrawn/steered and positioner 830. Accordingly, various parameters, such as the scanning path, the scan rate, and/or the number of scans, may be preprogrammed within a processor, such as processor 330, to automatically or remotely control sensor 800 using positioner 830. The processor may receive position information from a sensor system such as sensor detection system 318, to provide an output signal indicating the position of sensor 800 at a given point in time. Based on this signal, the processor may generate a map of temperature and/or applied heat as a function of position. The map is used to determine the heat flux at each point in the measurement range.

Although the embodiments depicted in FIGS. 3-8 illustrate the determination of heat flux in one dimension (i.e., along an elongate axis of the distributed temperature sensor), it is to be understood that various alternatives are possible. In particular, the embodiments depicted in FIGS. 3-8 may be adapted to generate a heat flux map of a two dimensional area and/or a three dimensional volume. For example, heat flux sensor system 300 may include a plurality of heat flux sensors, such as heat flux sensors 300-600, that are inserted at different angles and/or positions throughout the body tissue. Similarly, heat flux sensor system 300 may include one or more curved and/or flexible heat flux sensors. In some embodiments, a heat flux sensor may be scanned in two or three dimensions.

Figure 9:
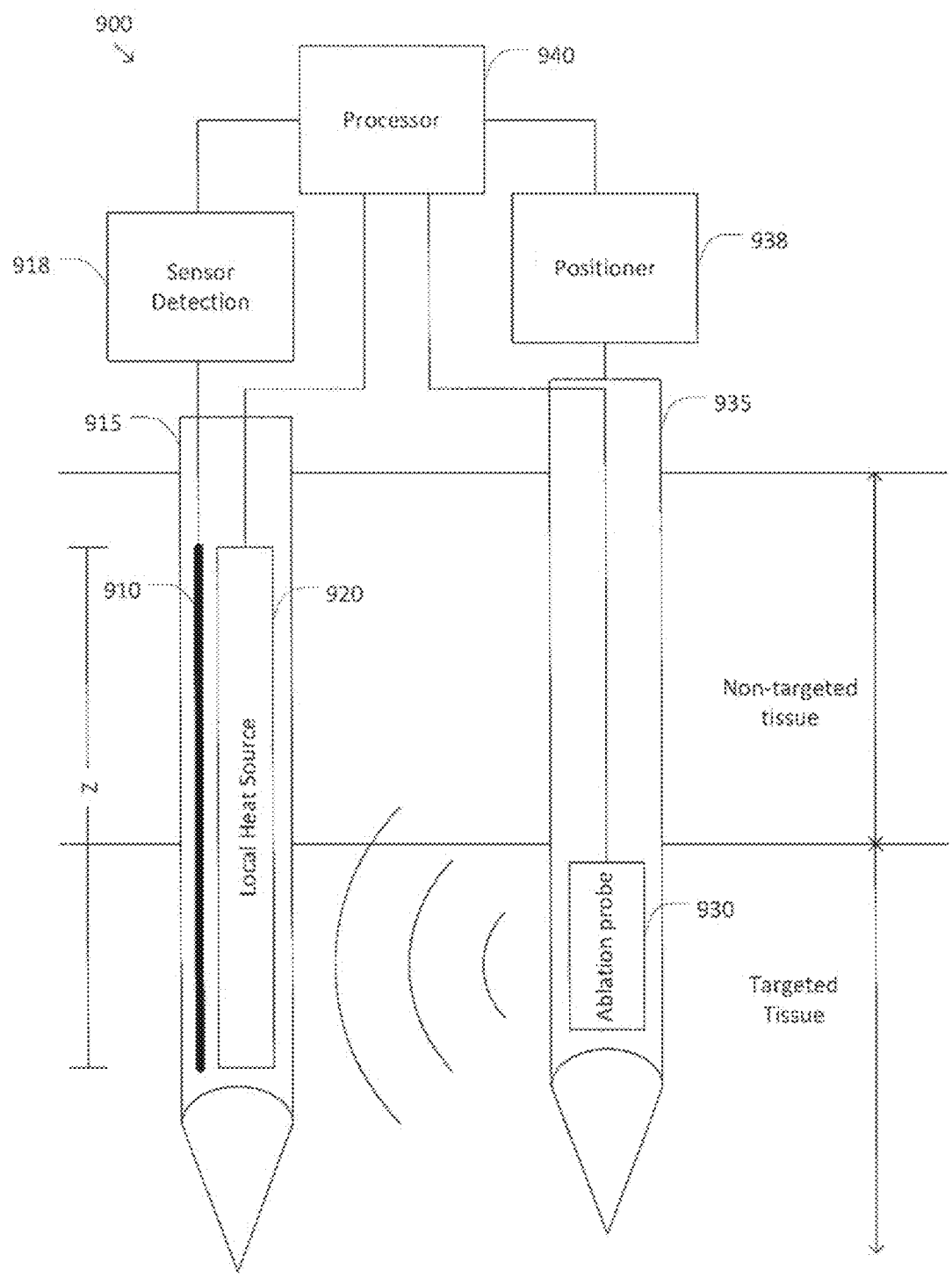
FIG. 9 is a simplified diagram of an ablation system using a distributed heat flux sensor according to some embodiments.

FIG. 9 is a simplified diagram of an ablation system 900 using a distributed sensor according to some embodiments. During an ablation procedure, ablation system 900 applies ablation energy (e.g., thermal, chemical, and/or mechanical energy) to destroy targeted tissue (e.g., cancerous tissue or cancerous tissue and a defined volume of non-cancerous or healthy tissue surrounding the cancerous tissue) while attempting to minimize the impact of the procedure on non-targeted tissue (e.g., non-cancerous tissue, blood vessels, surrounding organs, and the like).

Ablation system 900 includes a distributed sensor 910, an instrument 915, and a sensor detection system 918, which generally correspond to temperature sensor 310, instrument 315, and sensor detection system 318, as discussed previously with respect to FIG. 3. Distributed sensor 910 is placed in or near the targeted tissue to monitor spatial and/or temporal variations in temperature within a measurement range during the ablation procedure. For example, as depicted in FIG. 9, the measurement range Z spans a portion of non-targeted tissue and targeted tissue. Ablation system 900 may also include a local heat source 920, which generally corresponds to local heat source 320, as discussed previously with respect to FIG. 3.

Ablation system 900 includes an ablation probe 930 that delivers ablation energy to the targeted tissue. For example, ablation probe 930 may include a source of radio frequency energy, microwave radiation, ultrasonic energy, laser energy, direct heat energy and/or the like which heats up the targeted tissue. In some examples, ablation probe 930 may include a cryoprobe which freezes the targeted tissue. When ablation probe 930 includes a source of thermal energy (e.g., an RF/microwave source, direct heat source and/or a cryotherapeutic probe), ablation probe 930, rather than local heat source 920, may be used to locally heat the body tissue in the measurement range of distributed sensor 910. In some examples, ablation probe 930 may include a chemical delivery system to perform chemical ablation but may then require local heat source 920.

Ablation probe 930 may be mounted to an instrument 935. The position of instrument 935 may be controlled using a positioner 938 such as manipulator assembly 102 or drive unit 204. For example, positioner 938 may include a teleoperated actuation mechanism for inserting and/or withdrawing ablation probe 920. Although not depicted in FIG. 9, the position of instrument 915 may likewise be controlled using a separate positioner or positioner 938. In some examples, ablation probe 920 and/or instrument 915 may be positioned manually.

A processor 940 is coupled to receive temperature information from sensor detection system 918. For example, processor 940 may receive the measured temperature at a plurality of points in the measurement range. Processor 940 may also determine an amount of heat applied by local heat source 920 and/or ablation probe 930. Based on the measured temperature and applied heat, processor 940 may determine the heat flux at each of the plurality of points in the measurement range. The determined heat flux may be used to distinguish between ablated and non-ablated tissue. For example, the heat flux may change based on the biological state of the tissue (e.g., alive or dead), the chemical and/or structural properties of the tissue, whether the tissue is desiccated, and/or the like. In some examples, processor 940 may also determine a three-dimensional position of each temperature measurement in a known reference frame, e.g., by using shape data provided by a distributed sensor 910.

Based on the heat flux information, processor 940 generates one or more monitoring and/or feedback signals. For example, processor 940 may generate a monitoring signal corresponding to a plot of heat flux as a function of position. The plot may be displayed to a user via a display interface (such as display 340). Additionally or alternately, processor 940 may generate a monitoring signal corresponding to a two or three dimensional map of heat flux in a volume of tissue. Given three-dimensional position information of temperature measurements, the heat flux map location, position, and/or orientation can be associated with a known reference frame. Registration of the heat flux map reference frame with a tissue volume (e.g. patient) reference frame and/or imaging reference frame, the heat flux map may be superimposed on images of the patient's body and may identify the state of the tissue at one or more points in the image.

In some examples, processor 940 may generate a position feedback signal to adjust the position of ablation probe 920. For example, processor 940 may send the position feedback signal to positioner 930 to automatically increase or decrease the depth of ablation probe 920 when the heat flux information indicates that ablation probe 920 is not within the targeted tissue and/or is too close to the non-targeted tissue.

According to some embodiments, processor 940 may generate a power feedback signal to adjust the output power of ablation probe 920. For example, processor 940 may send the power feedback signal to ablation probe 920 to automatically adjust the amount of ablation energy supplied by ablation probe 920 when the heat flux information indicates that the heat flux of the targeted and/or non-target tissue is outside of a desired range. The power feedback signal is based on real-time heat flux information and therefore offers improved performance relative to setting the output power of ablation probe 920 using "rules of thumb" or other estimation methods.

According to some embodiments, processor 940 may generate a cutoff signal to terminate a stage of the ablation procedure (e.g., to end the procedure or move to the next stage of a multi-stage procedure) when a threshold condition is satisfied. For example, processor 940 may send the cutoff signal to ablation probe 920 to automatically stop providing power when a threshold level of ablation energy has been delivered to the targeted tissue, when the heat flux of the targeted tissue indicates that the tissue has been successfully ablated, when the heat flux of the non-targeted tissue deviates from a predetermined acceptable range, and/or the like. Like the power feedback signal, the cutoff signal is based on real-time information and therefore offers improved performance relative to setting the duration of the ablation procedure using "rules of thumb" or other estimation methods.

Although ablation system 900 has been described as automatically responding to feedback signals from processor 940, it is to be understood that other alternatives are possible. For example, one or more feedback signals, such as the position feedback signal, power feedback signal, and/or cutoff signal, may be displayed to a user (e.g., providing an alert or message via display 340). Consistent with such embodiments, the decision of how to respond to the feedback signals may be made by the user rather than being made automatically.

Moreover, although the feedback signals from processor 940 have been described as being determined based on heat flux, the feedback signals may additionally or alternately be determined directly from the temperature measurements received from distributed sensor 910. For example, the cutoff signal may be triggered when the temperature of the targeted and/or non-targeted tissue exceeds a predetermined threshold. Consistent with such embodiments, local heat source 920 may be omitted in some examples.

Figure 10:
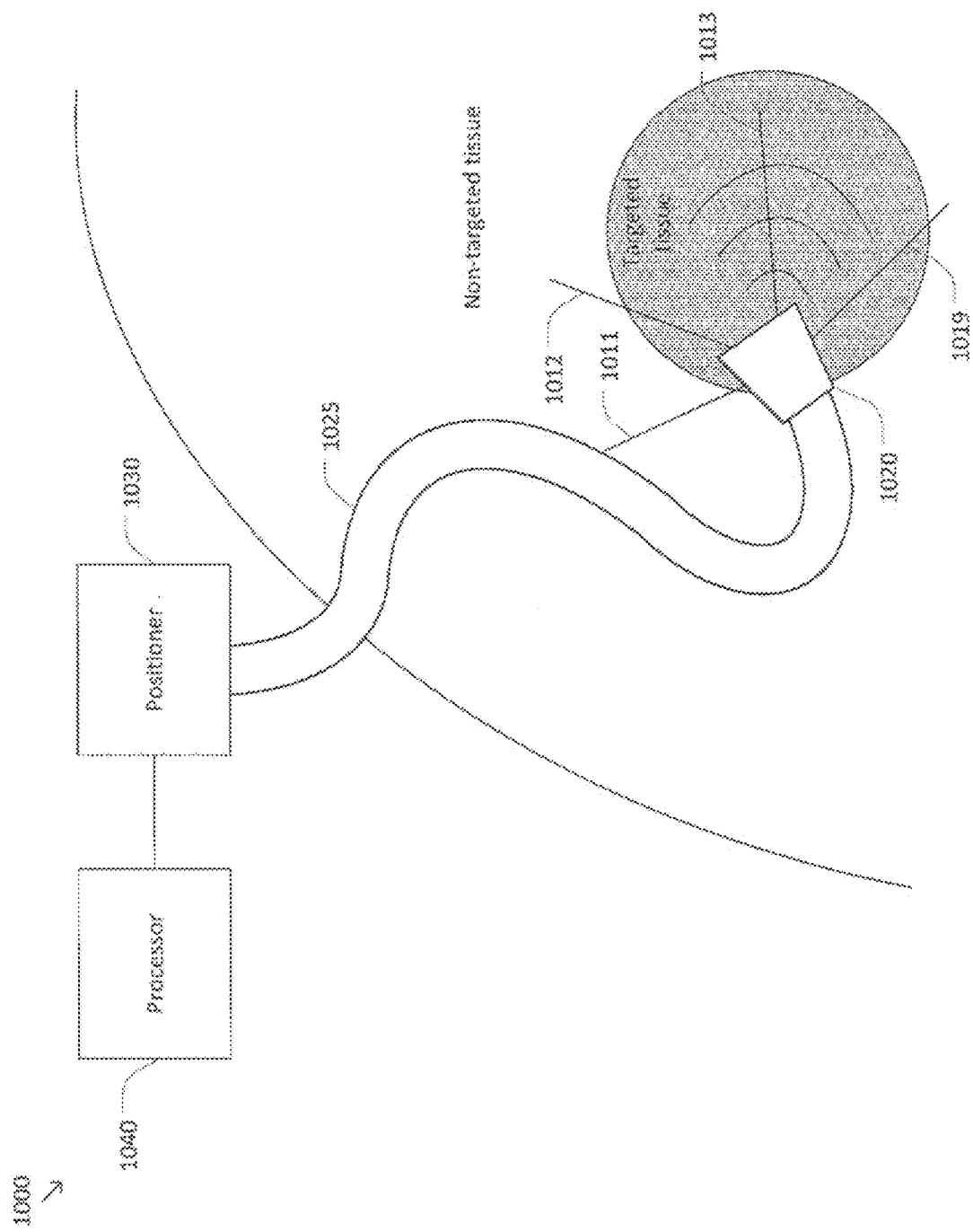
FIG. 10 is a simplified diagram of an ablation system using a plurality of distributed heat flux sensors according to some embodiments.

According to some embodiments, FIG. 10 is a simplified diagram of an ablation system 1000 including a plurality of distributed heat flux sensors 1011-1019, an ablation probe 1020, and a catheter 1025. The plurality of distributed heat flux sensors 1011-1019 are deployed radially from the catheter 1025 or the ablation probe 1020. Ablation probe 1020 applies ablation energy (e.g., thermal, chemical, and/or mechanical energy) to destroy targeted tissue while leaving non-target tissue substantially intact. According to some embodiments, ablation probe 1020 may deliver the ablation energy anisotropically. Consistent with such embodiments, the spatial distribution of the ablation energy provided by ablation probe 1020 may be adjustable. For example, the spatial distribution may be adjusted by changing the orientation of ablation probe 1020 using a positioner 1030 and/or a processor 1040.

Ablation probe 1020 is positioned at the distal end of a flexible catheter 1025, such as elongate device 202, or delivered through a lumen of flexible catheter 1025 to be positioned at the distal end of flexible catheter 1025. Flexible catheter 1025 may be navigated through anatomical passageways (e.g. respiratory, digestive, reproductive passageways) or through vasculature, to access the targeted tissue. In some examples, flexible catheter 1025 and/or ablation probe 1020 may be steerable. When ablation probe 1020 reaches the vicinity of the targeted tissue, one or more of distributed heat flux sensors 1011-1019 may be deployed through the lumen or one or more additional lumens of flexible catheter 1025 or one or more additional lumens of the ablation probe 1020. During an ablation procedure, processor 1040 receives heat flux information from distributed heat flux sensors 1011-1019. Based on the heat flux information, processor 1040 may provide feedback to adjust the spatial distribution of ablation energy provided by ablation probe 1020. For example, as depicted in FIG. 10, ablation energy from ablation probe 1020 is delivered in the direction generally oriented towards distributed heat flux sensor 1013, which extends through the center of the targeted tissue, and away from distributed heat flux sensor 1011, which mostly extends through non-targeted tissue. In this manner, the real-time feedback provided by distributed heat flux sensors 1011-1019 improves the performance of ablation system 1000 by more effectively directing the ablation energy from ablation probe 1020 to the targeted tissue.

According to some embodiments, one or more feedback signals may be displayed to a user (e.g., via display 340). In some examples, the one or more feedback signals may include a two or three dimensional, real-time map of tissue temperature that uses interpolation to estimate tissue temperature in regions between the distributed heat flux sensors 1011-1019. In some examples, the real-time map may be registered with images of the patient's anatomy, e.g., using three-dimensional shape data provided by distributed heat flux sensors 1011-1019, and overlaid on the images for display. Consistent with such embodiments, the decision of how to respond to the feedback signals may be made by the user rather than being made automatically.

Figure 11:
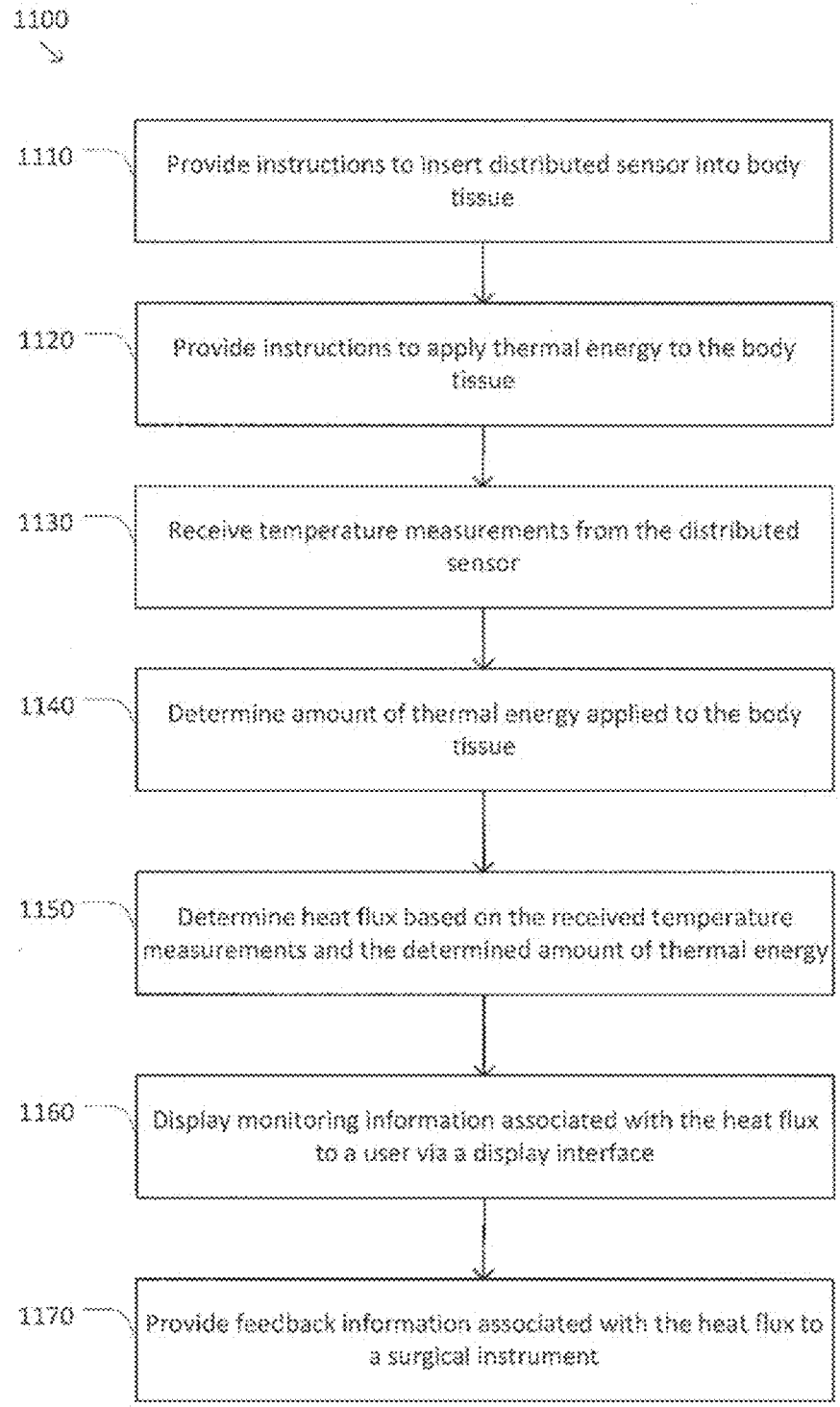
FIG. 11 is a simplified diagram of a method of determining heat flux according to some embodiments.

FIG. 11 is a simplified diagram of a method 1100 of determining heat flux according to some embodiments. In some embodiments consistent with FIG. 3, method 1100 may be performed during the operation of a distributed heat flux sensor system, such as distributed heat flux sensor system 300. In particular, method 1100 may be executed by a processor of the distributed heat flux sensor system, such as processor 330.

At a process 1110, instructions to insert a distributed sensor, such as distributed sensor 310, into a body tissue are provided to a positioning module. For example, the positioning module may include a teleoperational assembly that is coupled to the distributed sensor. In some embodiments, the distributed sensor may be an elongate temperature sensor, such as an OFDR-based fiber optic sensor, that measures temperature at a plurality of points in a measurement range in a batch mode (e.g., the temperatures at each of the plurality of points are measured concurrently and/or without physically repositioning the temperature sensor). In some embodiments, the distributed sensor may be a point temperature sensor, such as an EFPI-based temperature sensor, that measures temperature in the measurement range in a scanning mode, i.e., by moving through the measurement range. Consistent with such embodiments, the instructions that are transmitted to the positioning module may include scanning parameters, such as the scanning path, the scan rate, and/or a number of scans. In some examples, process 1110 may be omitted, such as when the distributed sensor is manually inserted into the body tissue.

At a process 1120, instructions to apply heat (or other thermal energy) to the body tissue are provided to a heat source. The instructions may specify a desired heat or power level, a desired current level, and/or the like. In response to the instructions, the heat source applies heat to cause a measurable change in the temperature of body tissue positioned within a detectable range of the distributed sensor (e.g., within 2 mm of the distributed sensor). The heat may be applied using a local and/or a remote heat source. For example, the local heat source may include a conductive cladding around the distributed sensor that is heated by applying electric current through the cladding. In some examples, the distributed sensor itself may be heated locally. For example, when the distributed sensor includes a fiber optic sensor, heating illumination may be applied through the optical fiber (e.g., a cladding and/or a core of the optical fiber) to cause it to heat up, as discussed previously with respect to FIG. 3. A remote heat source may include a source of radio frequency or microwave radiation, such as an RF ablation probe, and/or a microwave or ultrasonic transducer. In some examples, process 1120 may be omitted, such as when the heating source is operated manually.

At a process 1130, a plurality of temperature measurements corresponding to a plurality of points within the measurement range of the distributed sensor are received from the distributed sensor and/or a sensor detection system coupled to the distributed sensor, such as sensor detection systems 318 and/or 918. The plurality of temperature measurements may be received concurrently and/or sequentially and separately. For example, a fiber optic sensor may be operated to provide temperature measurements at each of the plurality of points at substantially the same time. By contrast, an EFPI-based temperature sensor may acquire the temperature measurements over time as the temperature probe is inserted and/or withdrawn from the body tissue. In some examples, a three-dimensional position of each of the plurality of points may be determined at process 1130. For example, the distributed sensor may be a fiber optic sensor configured to concurrently measure three-dimensional shape and temperature along the length of the sensor. The three-dimensional shape information received from the distributed sensor may be used to determine the three-dimensional position of each of the plurality of points.

At a process 1140, an amount of heat applied by the heat source at each of the plurality of points is determined. In some examples, the amount of heat may be determined based on information received from the heat source, such as a signal indicating the output power level. In some examples, the amount of applied heat may be a preset value and/or a user-selected value. In some examples, the amount of heat may be determined based on the instructions transmitted to the heat source at process 1120.

At a process 1150, the heat flux of the body tissue is determined at the plurality of points based on the received temperature measurements and the determined amount of applied heat. According to some embodiments, the heat flux may be determined based on the maximum amount of heat that can be applied to the tissue without a corresponding rise in the temperature of the tissue. That is, the heat flux is determined based on the point where the amount of heat applied to an affected volume of tissue by the heat source matches the amount of heat being conducted away from the affected volume by the tissue.

At a process 1160, monitoring information associated with the heat flux is displayed to a user via a display interface. In some examples, the monitoring information may include a plot of heat flux as a function of position. In some examples, the monitoring information may include an identification of the tissue type at each of the plurality of points. For example, the tissue type may be identified as cancerous or non-cancerous, ablated or healthy, and/or the like. Based on the identification of tissue type, the location of blood vessels or other anatomical features may be identified. In some examples, the tissue type may be determined by querying a database (or other data structure) to determine the tissue type that matches a given heat flux. In some examples, three-dimensional position information determined at process 1140 may be used to generate a three-dimensional heat flux map, register the heat flux map to a model and/or images of the patient's anatomy, and/or overlay the heat flux map onto the model and/or images. For example, the monitoring information may include enhanced images in which heat flux information is superimposed onto images of the patient anatomy.

At a process 1170, feedback information associated with the heat flux is provided to a surgical instrument. In some embodiments, the feedback information may be sent to a teleoperational surgical instrument. For example, the heat flux determined at process 1150 may indicate whether the teleoperational surgical instrument is correctly positioned and/or is having the desired impact on a given volume of body tissue. For example, the feedback information may indicate that the heat flux at a given point is outside of a desired range. In response to receiving the feedback information, the teleoperational surgical instrument may adjust its position and/or other operating parameters.

FIG. 12 is a simplified diagram of a method 1200 of providing feedback during a therapeutic procedure according to some embodiments. In some embodiments consistent with FIGS. 9-10, method 1200 may be performed during an ablation procedure carried out using an ablation system, such as ablation system 900 and/or 1000. In particular, method 1200 may be executed by a processor of the ablation system, such as processor 940 and/or 1040. However, it is to be understood that method 1200 is not limited to ablation applications and may be used in a wide variety of therapeutic procedures. For example, in embodiments consistent with FIG. 2, method 1200 may generally be used provide feedback to a medical instrument, such as medical instrument 226. As described previously, medical instrument 226 may include image capture probes, biopsy instruments, laser ablation fibers, and/or other surgical, diagnostic, or therapeutic tools.

At a process 1210, instructions to insert one or more distributed heat flux sensors, such as distributed heat flux sensors 1011-1019, into or near targeted tissue of the therapeutic procedure are transmitted to a positioning module. Process 1210 generally corresponds to processes 1110-1120 of method 1100. In some embodiments, the one or more distributed heat flux sensors may be projected radially outward through an elongate device, such as elongate device 202. In some examples, process 1210 may be omitted, such as when the distributed heat flux sensors are manually placed or where distributed heat flux sensors are integrated into an ablation probe.

At a process 1220, initial operating parameters of a therapeutic device (e.g., an ablation probe, such as ablation probe 920 and/or positioner 925) are provided to the therapeutic device. In some embodiments, the therapeutic device may be mounted to or delivered through the elongate device from which the distributed heat flux sensors are projected. The initial operating parameters may include positioning information, such as an insertion depth, orientation, catheter steering information, and/or the like. In some examples, where the therapeutic device includes an ablation probe, the initial operating parameters may specify a desired output power level of the ablation probe. In response to receiving the initial operating initial operating parameters, the ablation probe applies ablation energy (e.g., thermal, mechanical, and/or chemical energy) to the targeted tissue.

At a process 1230, a plurality of heat flux measurements are received from the one or more distributed heat flux sensors. The plurality of heat flux measurements reflect the impact of the therapeutic device on the targeted tissue and/or nearby or adjacent non-targeted tissue during the therapeutic procedure. For example, during an ablation procedure, the plurality of temperature measurements may indicate whether the ablation probe is properly oriented and/or set to the correct ablation energy output.

At a process 1240, adjusted operating parameters are provided to the therapeutic device and/or to the positioner. The adjusted operating parameters are determined based on the plurality of heat flux measurements received at process 1230. For example, during an ablation procedure, when the plurality of heat flux measurements indicate that a given volume of tissue is being ablated at a rate outside of a desired range (e.g., too slowly or too rapidly), the adjusted operating parameters may increase or decrease the ablation energy output of the ablation probe to bring the ablation rate back to the desired range. Similarly, the position, orientation, and/or directionality of the ablation probe may be adjusted to more precisely target the targeted tissue versus the non-targeted tissue. In some examples, the adjusted operating parameters may include stopping the ablation procedure and/or moving to a next stage of the ablation procedure when a threshold condition has been satisfied. For example, the plurality of heat flux measurements may indicate that the targeted tissue has been successfully ablated, or that the non-target tissue has deviated from an acceptable heat flux range. In some examples, determining whether the targeted tissue has been successfully ablated may be performed by comparing a current heat flux measurement to a baseline heat flux measurement captured at the beginning of the ablation procedure.

Figure 13:
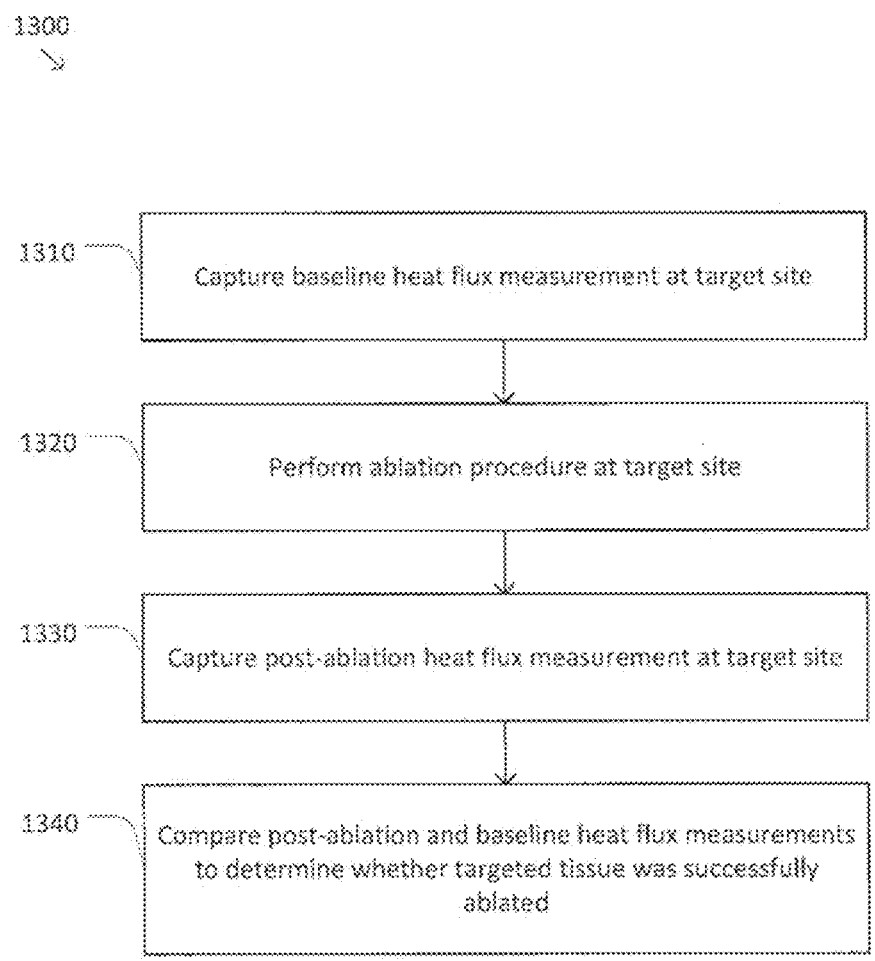
FIG. 13 is a simplified diagram of a method for detecting ablated tissue according to some embodiments.

FIG. 13 is a simplified diagram of a method 1300 of detecting ablated tissue according to some embodiments. In some embodiments consistent with FIGS. 9-10, method 1200 may be performed before, during, and/or after an ablation procedure carried out using an ablation system, such as ablation system 900 and/or 1000. In particular, method 1300 may be executed by a processor of the ablation system, such as processor 940 and/or 1040. The ablation procedure may be configured to ablate tissue, such as cancerous tissue, at a target site.

At a process 1310, a baseline heat flux measurement is captured at the target site. The baseline heat flux measurement may be captured using a distributed heat flux sensor, such as the distributed heat flux sensors depicted in FIGS. 3-11. In some examples, the distributed heat flux sensor may be integrated with an ablation probe (e.g., the heat flux sensor and the ablation probe may be mounted to the same instrument). In some examples, the distributed heat flux sensor and the ablation probe may be separate.

At a process 1320, an ablation procedure is performed at the target site. The ablation procedure may use an ablation probe that applies thermal, chemical, and/or mechanical ablation energy to ablate tissue at the target site. In some examples, the amount of ablation energy, the location of the target site relative to the ablation probe, the sensitivity of the targeted tissue to the ablation energy, and/or the like may not be known with certainty. Accordingly, various parameters of the ablation procedure, such as the position of the ablation probe, the output power level, the ablation time, and/or the like, may be selected based on estimates, empirical data and/or "rules of thumb."

At a process 1330, a post-ablation heat flux measurement is captured at the target site. For example, the post-ablation heat flux measurement may be captured in substantially the same manner as the baseline heat flux measurement. In some examples, the heat flux sensor used at process 1310 may be withdrawn from the target site during the ablation procedure of process 1320 and reinserted during process 1330. In other examples, the heat flux sensor may remain at the target site throughout processes 1310-1330.

At a process 1340, the post-ablation heat flux measurement is compared to the baseline heat flux measurement to determine whether the targeted tissue was successfully ablated. In some examples, ablated tissue may be detected based on a difference between the post-ablation and baseline heat flux measurements. For example, a substantial increase in the heat flux at a given location may indicate that the tissue has been ablated. When the target tissue is determined to have been successfully ablated, the ablation procedure may be terminated. However, when all or a portion of the targeted tissue has not been successfully ablated, method 1300 may return to process 1320 to continue the ablation procedure until all of the targeted tissue is successfully ablated. The ability to repeat process 1320 until the targeted tissue is successfully ablated may allow the operating parameters used during process 1320 to be selected more conservatively than a single shot approach, resulting in less impact on non-targeted tissue, while ensuring complete ablation of the targeted tissue.

Some examples of processors, such as processor 330, 940, and/or 840 may include non-transient, tangible, machine readable media that include executable code that when run by one or more processors (e.g., processors 330, 940, and/or 1040) may cause the one or more processors to perform the processes of methods 1100-1300. Some common forms of machine readable media that may include the processes of methods 1100-1300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system for distributed heat flux sensing of body tissue, the system comprising:
   a flexible elongate device comprising a distributed sensor that provides a plurality of temperature measurements corresponding to a plurality of points in a measurement range, the distributed sensor extending through the measurement range;
   a thermal energy source that applies thermal energy to the body tissue along the measurement range; and
   one or more processors configured to:
      receive the plurality of temperature measurements from the distributed sensor, the plurality of temperature measurements corresponding to the plurality of points;

determine a location of the plurality of points based on data from the distributed sensor of the flexible elongate device in a known three-dimensional reference frame;

determine an amount of thermal energy applied by the thermal energy source; and determine heat flux at each of the plurality of points based on the location of the plurality of points, the plurality of temperature measurements, and a maximum amount of thermal energy applied by the thermal energy source without a corresponding rise in temperature being indicated by the plurality of temperature measurements.

2. The system of claim 1, wherein the distributed sensor measures temperature at the plurality of points in a batch mode or a scanning mode.

3. The system of claim 1, wherein the thermal energy source includes a conductive cladding around the distributed sensor that applies heat upon application of electric current.

4. The system of claim 3, wherein the conductive cladding is configured as:

a body electrode to electrically couple the conductive cladding to the body tissue;

a pair of concentric metal tubes that are electrically joined at a distal end of the conductive cladding; or an insulating capillary tube coated by a conductive layer.

5. The system of claim 1, wherein the distributed sensor comprising a fiber optic sensor including an optical fiber and the one or more processors are further configured to generate a heat flux map based on the location of the plurality of points determined based on shape data from the fiber optic sensor.

6. The system of claim 5, wherein the shape data is based on a determination of at least one of a position or an orientation of the fiber optic sensor in the known three-dimensional reference frame.

7. The system of claim 6, wherein the one or more processors are further configured to:

register an anatomical model or image of the body tissue to the three-dimensional reference frame;

overlay the heat flux map on the anatomical model or image of the body tissue based on the determination of the at least one of the position or the orientation of the fiber optic sensor in the three-dimensional reference frame; and display the anatomical model or the image of the body tissue with the overlay of the heat flux map.

8. The system of claim 1, wherein the one or more processors are further configured to identify a type of tissue at each of the plurality of points based on the determined heat flux.

9. The system of claim 8, wherein the one or more processors are further configured to classify the type of tissue as at least one of cancerous, non-cancerous, ablated, non-ablated, or healthy based on the determined heat flux.

10. The system of claim 8, wherein the one or more processors are further configured to:

identify the type of tissue as a blood vessel; and determine a location of the blood vessel.

11. The system of claim 1, further comprising a display that is coupled to the one or more processors, wherein the display depicts at least one of a visual representation of the determined heat flux or an operating parameter during an operational procedure.

12. The system of claim 1, further comprising a therapeutic tool, wherein the one or more processors are further configured to alter an operating parameter of the therapeutic tool based on the determined heat flux.

13. The system of claim 12, wherein the therapeutic tool is an ablation probe.

14. The system of claim 12, wherein the operating parameter includes at least one of a position of the therapeutic tool, an output power of the therapeutic tool, or a termination of a stage of a procedure when a threshold condition is satisfied.

15. The system of claim 12, wherein the therapeutic tool is mounted to or inserted through the flexible elongate device.

16. A method for determining heat flux of body tissue using a distributed sensor of a flexible elongate device, the method comprising:

receiving a plurality of temperature measurements from the distributed sensor of the flexible elongate device, wherein the plurality of temperature measurements correspond to a plurality of points in a measurement range through which the distributed sensor extends;

determining a location at the plurality of points based on data from the distributed sensor of the flexible elongate device in a known three-dimensional reference frame;

determining an amount of applied thermal energy; and determining a heat flux of the body tissue at the plurality of points based on the location of the plurality of points, the received plurality of temperature measurements, and a maximum amount of applied thermal energy without a corresponding rise in temperature being indicated by the plurality of temperature measurements.

17. The method of claim 16, wherein the heat flux of the body tissue at the plurality of points is determined during a therapeutic procedure that is performed based on initial operating parameters by a therapeutic tool; and the method further comprises:

providing adjusted operating parameters to the therapeutic tool based on the determined heat flux.

18. The method of claim 16, further comprising applying thermal energy to the body tissue to heat the body tissue.

19. The method of claim 18, wherein applying thermal energy comprises applying heating illumination through the distributed sensor or generating a standing electromagnetic wave in the distributed sensor to generate heat.

20. The method of claim 16, wherein the distributed sensor comprises a fiber optic sensor including an optical fiber.

* * * * *